(12) United States Patent
Rau et al.

(10) Patent No.: US 9,278,139 B2
(45) Date of Patent: *Mar. 8, 2016

(54) STERILIZATION OF BIODEGRADABLE HYDROGELS

(71) Applicant: Ascendis Pharma A/S, Hellerup (DK)

(72) Inventors: Harald Rau, Heidelberg (DE); Tobias Voigt, Heidelberg (DE); Ulrich Hersel, Heidelberg (DE)

(73) Assignee: Ascendis Pharma A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,291

(22) Filed: Jan. 26, 2015

(65) Prior Publication Data

US 2015/0196667 A1    Jul. 16, 2015

Related U.S. Application Data

(62) Division of application No. 13/505,214, filed as application No. PCT/EP2010/066404 on Oct. 28, 2010, now Pat. No. 8,986,609.

(30) Foreign Application Priority Data

Oct. 29, 2009    (EP) ..................................... 09174526

(51) Int. Cl.
| A61K 47/48 | (2006.01) |
| A61K 41/00 | (2006.01) |
| A61L 2/00  | (2006.01) |
| A61L 2/08  | (2006.01) |
| A61L 2/10  | (2006.01) |
| C08G 65/329 | (2006.01) |
| C08L 71/02 | (2006.01) |

(52) U.S. Cl.
CPC ....... *A61K 47/48784* (2013.01); *A61K 41/0019* (2013.01); *A61L 2/0035* (2013.01); *A61L 2/081* (2013.01); *A61L 2/10* (2013.01); *C08G 65/329* (2013.01); *C08L 71/02* (2013.01); *A61L 2202/21* (2013.01); *C08L 2203/02* (2013.01)

(58) Field of Classification Search
CPC .................. A61K 47/48784; A61K 41/0019; A61L 2/20; A61L 2/0035; A61L 2/081; A61L 2202/21; C08G 65/329; C08L 71/02; C08L 2203/02

See application file for complete search history.

(56) References Cited

U.S. PATENT DOCUMENTS

| 8,986,609 B2 * | 3/2015 | Rau et al. .................... 422/22 |
| 2004/0023842 A1 * | 2/2004 | Pathak et al. ................. 514/1 |
| 2007/0275030 A1 * | 11/2007 | Muratoglu et al. ........... 424/422 |

* cited by examiner

*Primary Examiner* — Shailendra Kumar
(74) *Attorney, Agent, or Firm* — Frommer Lawrence & Haug LLP

(57) ABSTRACT

The present invention relates to a terminal sterilization process for biodegradable PEG-based insoluble hydrogels using irradiation. The presence of a protective solvent ensures that the hydrogel remains intact with functionally preserved three-dimensional and physicochemical properties.

17 Claims, 12 Drawing Sheets

STERILIZATION OF BIODEGRADABLE HYDROGELS

The present application is a divisional of U.S. patent application Ser. No. 13/505,214 filed on Apr. 30, 2012, now U.S. Pat. No. 8,986,609, which claims priority from PCT Patent Application No. PCT/EP2010/066404 filed on Oct. 28, 2010, which claims priority from European Patent Application No. EP 09174526.5 filed on Oct. 29, 2009, the disclosures of which are incorporated herein by reference in their entirety.

BACKGROUND OF THE INVENTION

1. Field of the Invention

Biodegradable PEG-based hydrogels are of interest for various medical and pharmaceutical applications such as tissue regeneration, wound closure and drug delivery. For safety reasons it is strongly preferred in some applications, like for example drug delivery, to engineer biodegradability into the PEG hydrogel. Biodegradability may be introduced into a hydrogel by ester bonds that undergo spontaneous or enzymatic hydrolysis in the aqueous in vivo environment.

It is noted that citation or identification of any document in this application is not an admission that such document is available as prior art to the present invention.

Sterility of a pharmaceutical composition or a medical device intended for implantation or topical application is mandatory to receive approval as a correspondingly marketed product. Various methods of sterilization have been proposed, such as heat, pressure, filtering, chemicals or irradiation. Unfortunately, these sterilization methods are not applicable to biodegradable PEG-hydrogels as they are not compatible with retaining the hydrogel's structure and properties, thus limiting the medical use of biodegradable PEG-hydrogels.

For instance, injectable solutions are most often sterilized in their vials by autoclaving, but biodegradable bonds will undergo drastically accelerated degradation, if subjected to high temperature. Therefore, autoclaving a biodegradable PEG hydrogel will result in a pre-degraded material which will not qualify for therapeutical applications.

Alternatively, a solution may be sterilized by filtration using filters with pore sizes of 0.2 µm to remove any microbial contaminants and subsequently filling the sterile solution into the vials under aseptic conditions. However, in case of insoluble crosslinked PEG hydrogels, the material is not soluble, but may be present in form of a suspension of microparticles or as another three-dimensional object (e.g., disc or tube), typically larger in size than 0.2 µm and therefore such suspensions or gel objects cannot be sterilized by filtration.

The international patent application WO2003/035244 describes a closed-circuit apparatus which allows the preparation of sterile microparticles. Filter-sterilized chemical components are kept sterile within the aseptic environment of the system throughout the particle formation process, thus resulting in sterile microparticles.

Such aseptic processing, which applies a sterile filtration step at the level of the starting materials and maintains aseptic conditions during the process, has certain disadvantages over sterilization after the synthesis of the hydrogel, called terminal sterilization. The earlier the sterilization step occurs in the production process, the higher is the risk of accidental contamination. Aseptic processing also requires elaborate technical equipment, thus increasing production cost. Therefore, a terminal sterilization method is preferred.

Photodegradation with UV light and gamma irradiation of polymers generate radicals and/or ions that often lead to cleavage and cross-linking. Oxidation also occurs, complicating the situation, since exposure to light is seldom in the absence of oxygen. Generally, this changes the properties of the hydrogel and the material's susceptibility to biodegradation (Encyclopedia of Polymer Science and Technology, Mark Herman (Ed) Wiley, 2004, p. 263 ff).

Treatment with ethylene oxide gas or with solutions containing hydrogen peroxide will cause similar side reactions negatively affecting the hydrogel's biodegradation properties and causing substantial deviation of the degradation kinetics of the treated hydrogel as compared to the untreated hydrogel material. In addition, care has to be taken to ensure that no significant amounts of for example ethylene oxide remain in the hydrogel, which may be toxic and cause undesired side-effects.

To circumvent the difficulties associated with terminal sterilization, the processes of crosslinking and sterilization have been combined. U.S. Pat. No. 5,634,943 details a method for generating crosslinked PEG hydrogels by gamma irradiation. In this approach, linear PEG (MW 200 kDa) was dissolved in aqueous saline, degassed and irradiated by means of a gamma source such as Co60. A dosage of between 2.5 and 25 Mrads (equivalent to between 25 and 250 kGy) was sufficient to effect crosslinking of the PEG chains by radical formation and interchain linkage, resulting in a hydrated insoluble hydrogel. Due to the fact that the irradiation dosage was also sufficiently high for sterilization, in one step a material was obtained that was suitable for implantation into the cornea of the eye.

Similarly, US patent application US20090030102 describes a method of forming a crosslinked polymer gel for use in electronic devices, based on polyalkylene oxide, polyarylene oxide, or polyglycidyl ether, which in the presence of a crosslinker and organic solvent is crosslinked through UV and/or gamma irradiation.

For other applications, such as delivery of pharmaceuticals, biodegradability of the PEG hydrogel is desirable. U.S. Pat. No. 6,537,569 details a process of generating degradable PEG hydrogels through gamma irradiation. Here, linear PEG chains connected through biodegradable ester linkages are employed (MW 10 kDa). Irradiation with 25 or 30 kGy formed interchain crosslinks and an insoluble PEG hydrogel.

It was also attempted to control drug release kinetics by varying the degree of crosslinking in UV or gamma irradiated PEG hydrogels (Minkova et al., J. Polym. Sci., Polym. Phys. 27 (1989) 621-642, Belcheva et al., Macromol. Symp. 103 (1996) 193, Rosiak and Yoshii, Nuclear Instruments and Methods in Physics research B 151 (1999) 56-64, Rosiak and Ulansky, Radiation Physics and Chemistry 55 (1999) 139-151, Dimitrov et al., Acta Pharmaceutica Turcica 46 (2004) 49-54). Nevertheless, here the presence of drug during the irradiation process is required to provide for the entrapment of drug, but the possibility of irradation-caused side reactions such as oxidation or hydrolysis or conjugations to the polymer chains render this approach impractical for most therapeutic entities.

It has also been shown, that irradiation affects other properties of PEG-based hydrogels such as swelling and roughness (Kanjickal et al, J Biomed Mater Res A. 2008 Jan. 9—Effects of sterilization on poly(ethylene glycol) hydrogels).

Various PEG-based hydrogels have been described in the literature. For example, WO2006/003014 describes polymeric hydrogel conjugates of a prodrug, in which the hydrogel consists of non-biodegradable backbone moieties interconnected by crosslinkers comprising biodegradable bonds.

The European patent application EP09167026.5 describes a PEG-based hydrogel with a characteristic late-stage burst-like degradation kinetics.

A hydrogel which only consists of PEG-moieties is described in the European patent EP1019446. Hydrolytically unstable bonds are built into the hydrogel to allow degradation. The patent also claims the use of such hydrogel as a drug delivery system.

U.S. Pat. No. 5,514,379 describes, among others, PEG-based hydrogels which may contain diagnostic labels, alone or in combination with therapeutic drugs. Similarly, U.S. Pat. No. 6,602,952 describes PEG-chitosan hydrogels, containing biologically active agents which may be injected in vivo. The PCT application WO2006/38462 describes poly(ethylene oxide)-containing hydrogels with carbamate crosslinks which are used as drug delivery devices or in other biomedical functions.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of any previously described product, method of making the product, or process of using the product.

SUMMARY OF THE INVENTION

Although all of the above described hydrogels are meant to be used in applications that require sterility, this issue is not addressed by these patents or patent applications which limits their industrial applicability.

As a consequence of the shortcomings in hydrogel sterilization, insoluble crosslinked biodegradable PEG-based hydrogels are not yet approved as such, but only as precursor compositions that form a hydrogel in situ after administration (Corgel™ BioHydrogel, Focal® Technology). Therefore, there is a need to provide a means to terminally sterilize hydrogels in a cost-efficient and preserving way in order to fully utilize hydrogels in contamination-sensitive applications.

Thus, an object of the present invention is to provide an alternative method for insoluble biodegradable PEG-based hydrogel sterilization to at least partly overcome disadvantages and fulfill the needs as described above.

The object is achieved by a method for sterilizing a biodegradable poly(ethylene glycol) based insoluble hydrogel comprising backbone moieties which are interconnected by hydrolytically degradable bonds, comprising the steps of
(a) Providing the hydrogel;
(b) Solvating the hydrogel in a protective solvent or in a mixture of two or more protective solvents or aqueous solutions thereof;
(c) Subjecting the solvated hydrogel to gamma radiation.

It was now surprisingly discovered that pre-formed biodegradable PEG-based insoluble hydrogels may be sterilized by gamma radiation without damage to the labile biodegradable bonds and thus also no damage to the stable bonds and without causing crosslinking, if the irradiation with gamma rays was performed in the presence of a protective solvent, preferably N-methyl-2-pyrrolidone (NMP), DMA, DMF, or DMI, even more preferably, NMP.

In particular, in vitro degradation kinetics of such irradiated insoluble biodegradable PEG hydrogels according to the invention were identical to in vitro degradation kinetics of non-irradiated PEG hydrogels. Furthermore, such irradiated insoluble biodegradable PEG hydrogels were still fully degradable. If interchain crosslinks by radical formation had formed, the degradation kinetics would have been affected, and the insoluble biodegradable PEG hydrogel degradation process would be slower, the degradation curve would be flattened and the degradation might not go to completion.

In case the insoluble biodegradable PEG-based hydrogel contains functional groups, such groups are still functional after sterilization.

Within the present invention the terms used have the meaning as follows.

A hydrogel may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity.

The term "PEG-based hydrogels" ("PEG hydrogel") as understood herein means that the mass proportion of PEG chains in the hydrogel is at least 10% by weight, preferably at least 25%, based on the total weight of the hydrogel. The remainder can be made up of other polymers and other moieties.

The term polymer describes a molecule comprised of repeating structural units connected by chemical bonds in a linear, circular, branched, crosslinked or dendrimeric way or a combination thereof, which can be of synthetic or biological origin or a combination of both. Examples include, but are not limited, to poly(acrylic acids), poly(acrylates), poly(acrylamides), poly(alkyloxy)polymers, poly(amides), poly(amidoamines), poly(amino acids), poly(anhydrides), poly(aspartamide), poly(butyric acid), poly(caprolacton), poly(carbonates), poly(cyanoacrylates), poly(dimethylacrylamide), poly(esters), poly(ethylene), poly(ethylene glycol), poly(ethylene oxide), poly(ethyloxazoline), poly(glycolic acid), poly(hydroxyethyl acrylate), poly(hydroxyethyloxazoline), poly(hydroxypropylmethacrylamide), poly(hydroxypropyl methacrylate), poly(hydroxypropyloxazoline), poly(iminocarbonates), poly(N-isopropylacrylamide), poly(lactic acid), poly(lactic-co-glycolic acid), poly(methacrylamide), poly(methacrylates), poly(methyloxazoline), poly(propylene fumarate), poly(organophosphazenes), poly(ortho esters), poly(oxazolines), poly(propylene glycol), poly(siloxanes), poly(urethanes), poly(vinylalcohols), poly(vinylamines), poly(vinylmethylether), poly(vinylpyrrolidone), silicones, ribonucleic acids, desoxynucleic acid, albumins, antibodies and fragments thereof, blood plasma protein, collagens, elastin, fascin, fibrin, keratins, polyaspartate, polyglutamate, prolamins, transferrins, cytochromes, flavoprotein, glycoproteins, hemoproteins, lipoproteins, metalloproteins, phytochromes, phosphoproteins, opsins, agar, agarose, alginate, arabinans, arabinogalactans, carrageenan, cellulose, carbomethyl cellulose, hydroxypropyl methylcellulose and other carbohydrate-based polymers, chitosan, dextran, dextrin, gelatin, hyaluronic acid and derivatives, mannan, pectins, rhamnogalacturonans, starch, hydroxyalkyl starch, xylan, and copolymers and functionalized derivatives thereof.

"Intact" in relation to the sterilized hydrogel means that no damage to the labile biodegradable bonds and thus also no damage to the stable bonds and no detectable further crosslinking have occurred during sterilization. The "intactness" of the hydrogel can be measured by the in vitro degradation kinetics of biodegradable PEG-based hydrogels sterilized according to the invention and the level to which it is identical to the in vitro degradation kinetics of non-sterilized biodegradable PEG hydrogel. Furthermore, such irradiated biodegradable PEG hydrogels are still fully degradable. If interchain crosslinks by radical formation had formed, the degradation kinetics would have been affected, and the PEG hydrogel degradation process would be slower, the degradation curve would be flattened and the degradation might not go to completion. If cisions of chains occur, the PEG hydrogel degradation process would be accelerated. Preferably, the term "identical" in relation to two degradation kinetics means that the time needed to obtain a degradation of X % does not vary between the two degradation kinetics by more than 20%, preferably by no more than 15%, and wherein X is in the range of from 5 to 90.

If the biodegradable PEG-based hydrogel contains functional groups, these functional groups are preserved. For example, if the functional groups are amine groups, the amine content of the PEG-based hydrogel is the same before the sterilization and after the sterilization process. Preferably, the term "same" in this context means that the number of functional groups in a hydrogel sterilized according to the present invention varies from the number of functional groups in the hydrogel before sterilization by less than 30%, preferably by less than 20%.

To measure the degradation kinetics, aliquots of soluble backbone degradation products can be separated from the insoluble biodegradable PEG based hydrogel and can be quantified without interference from other soluble degradation products released from the hydrogel. A hydrogel object may be separated from excess water of buffer of physiological osmolality by sedimentation or centrifugation. Centrifugation may be performed in such way that the supernatant provides for at least 10% of the volume of the swollen hydrogel. Soluble hydrogel degradation products remain in the aqueous supernatant after such sedimentation or centrifugation step, and water-soluble degradation products comprising one or more backbone moieties are detectable by subjecting aliquots of such supernatant to suitable separation and/or analytical methods.

Alternatively, water-soluble degradation products may be separated from water-insoluble degradation products by filtration through 0.45 μm filters, after which the water-soluble degradation products can be found in the flow-through. Water-soluble degradation products may also be separated from water-insoluble degradation products by a combination of a centrifugation and a filtration step.

For instance, the backbone moieties may carry groups that exhibit UV absorption at wavelengths where other degradation products do not exhibit UV absorption. Such selectively UV-absorbing groups may be structural components of the backbone moiety such as amide bonds or may be introduced into the backbone by attachment to its reactive functional groups by means of aromatic ring systems such as indolyl groups.

To enhance physicochemical or pharmacokinetic properties of a drug in vivo, such drug can be conjugated with a carrier, for example, a hydrogel. If the drug is transiently bound to a carrier and/or a linker, such systems are commonly assigned as carrier-linked prodrugs. According to the definitions provided by IUPAC (as given under http://www.chem.qmul.ac.uk/iupac.medchem, accessed on Jul. 22, 2009), a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The terms "drug," "biologically active molecule," "biologically active moiety," "biologically active agent," "active agent", and the like mean any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs (e.g., nonpeptidic drugs), dyes, lipids, nucleosides, oligonucleotides, polynucleotides, nucleic acids, cells, viruses, liposomes, microparticles and micelles. Classes of biologically active agents that are suitable for use with the invention include, but are not limited to, hypnotics and sedatives, psychic energizers, tranquilizers, respiratory drugs, anticonvulsants, muscle relaxants, antiparkinson agents (dopamine antagnonists), analgesics, anti-inflammatories, anti-allergics, antianxiety drugs (anxiolytics), appetite suppressants, antiobesity drugs, antimigraine agents, muscle contractants, anti infectives (antibiotics, antivirals, antifungals, antibacterials, vaccines) anti-inflammatory, antiarthritics, antimalarials, antiemetics, anepileptics, antidiabetics, bronchodilators, cytokines, growth factors, anti-cancer agents, anticoagulants, antihypertensives, cardiovascular drugs, vasodilating, vasoconstricting, antiarrhythmics, antioxicants, anti-asthma agents, central nervous system-active agents, hormonal agents including contraceptives, immunomodulating agents, sympathomimetics, diuretics, lipid regulating agents, antiandrogenic agents, antiparasitics, anticoagulants, neoplastics, antineoplastics, hypoglycemics, steroidal agents, nutritional agents and supplements, growth supplements, antienteritis agents, vaccines, antibodies, diagnostic agents, contrasting agents, and the like.

"Small molecule biologically active moiety" refers to any of the above described biologically active moieties with a molecular weight of 3000 Dalton or less.

Biodegradability of the hydrogels for the method according to the present invention is achieved by introduction of hydrolytically degradable bonds.

The term "biodegradable" within the context of the present invention refers to linkages which are non-enzymatically hydrolytically degradable under physiological conditions (aqueous buffer at pH 7.4, 37° C.) with half-lives ranging from one hour to three months, and which include, but are not limited to, aconityls, acetals, carboxylic anhydrides, carboxylic esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are carboxylic esters, carbonates, phosphoesters and sulfonic acid esters and most preferred are carboxylic esters or carbonates. It is understood that for in vitro studies accelerated conditions like, for example, pH 9, 37° C., aqueous buffer, may be used for practical purposes.

Accordingly, hydrolytically degradable bonds are, for example, aconityls, acetals, carboxylic anhydrides, carboxylic esters, imines, hydrazones, maleamic acid amides, ortho esters, phosphamides, phosphoesters, phosphosilyl esters, silyl esters, sulfonic esters, aromatic carbamates, combinations thereof, and the like. Preferred hydrolytically degradable bonds are carboxylic esters, carbonates, phosphoesters and sulfonic acid esters and most preferred are carboxylic esters or carbonates.

The term "interrupted" means that a urea, amide, or carbamate group or ether is inserted between two carbons of a carbon chain.

"Non-biodegradable" (stable) refers to linkages which are non-cleavable permanent bonds meaning that the respective connecting moiety has a half-life of at least six months under physiological conditions (aqueous buffer at pH 7.4, 37° C.).

"Sustained release delivery systems" refer to compositions that release a drug into the body of a patient over an extended period of time.

"Surgical sealant" or "medical sealant" refers to hydrogel-based glues and other means to close wounds, such as incisions, lacerations, punctures, abrasions, contusions or avulsions.

"Hemostatic agents" refer to agents used to arrest bleeding from wounds.

"Surgical sponges" mean sponges used to absorb liquids from a surgical site.

Gamma radiation is defined as electromagnetic radiation with quantum energy of more than 200 keV, independent of its radiation source. Preferably, the radiation source is cobalt 60.

"Sterile" means the absence of any detectable transmissible agents, including bacteria, yeasts, fungi, viruses, spores, in all developmental stages and forms.

"Sterilization process" refers to a procedure to render a material sterile, for example by irradiation, such as irradiation with UV- or gamma rays. Preferably, irradiation with gamma rays is used.

"Protective solvent" describes a chemical compound used to solvate the dry hydrogel before sterilization to preserve the three-dimensional structure and physicochemical properties, and thus the intactness of the hydrogel.

DETAILED DESCRIPTION OF EMBODIMENTS

Figure 1A:
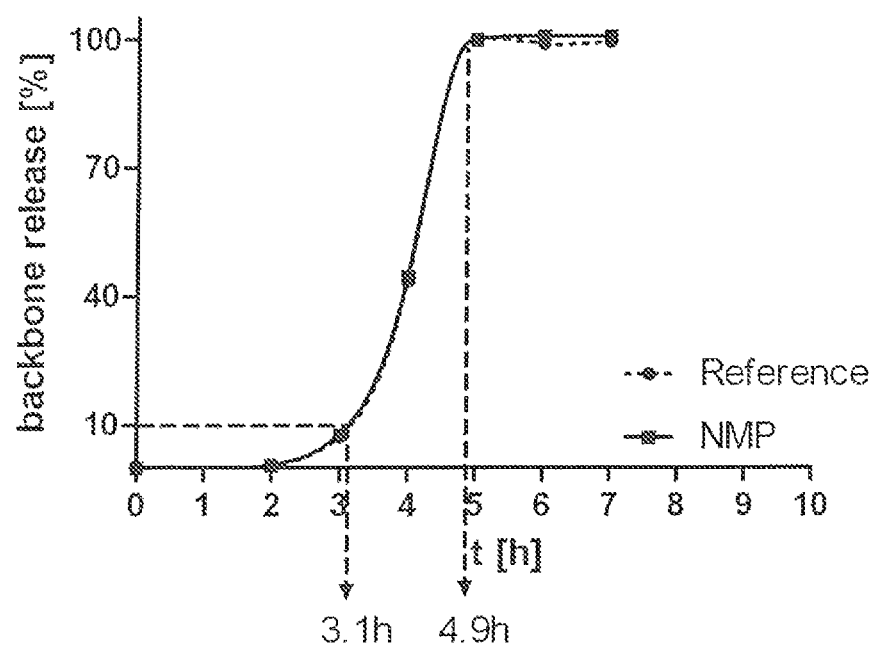
FIGS. 1a-1k shows the in vitro degradation kinetics of 4a (FIG. 1a), 4b (FIG. 1b), 4c (FIG. 1c), 4d (FIG. 1d) and 4e (FIG. 1e) after sterilization, each together with 3a (unsterilized hydrogel; "reference"), at pH 10.3, 37° C., and 4f (FIG. 1f), 4g (FIG. 1g), 4h (FIG. 1h), 4i (FIG. 1i), 4j (FIG. 1j) and 4k (FIG. 1k) after sterilization, each together with 3b (unsterilized hydrogel; "reference"), at pH 9.0, 37° C.
Figure 1B:
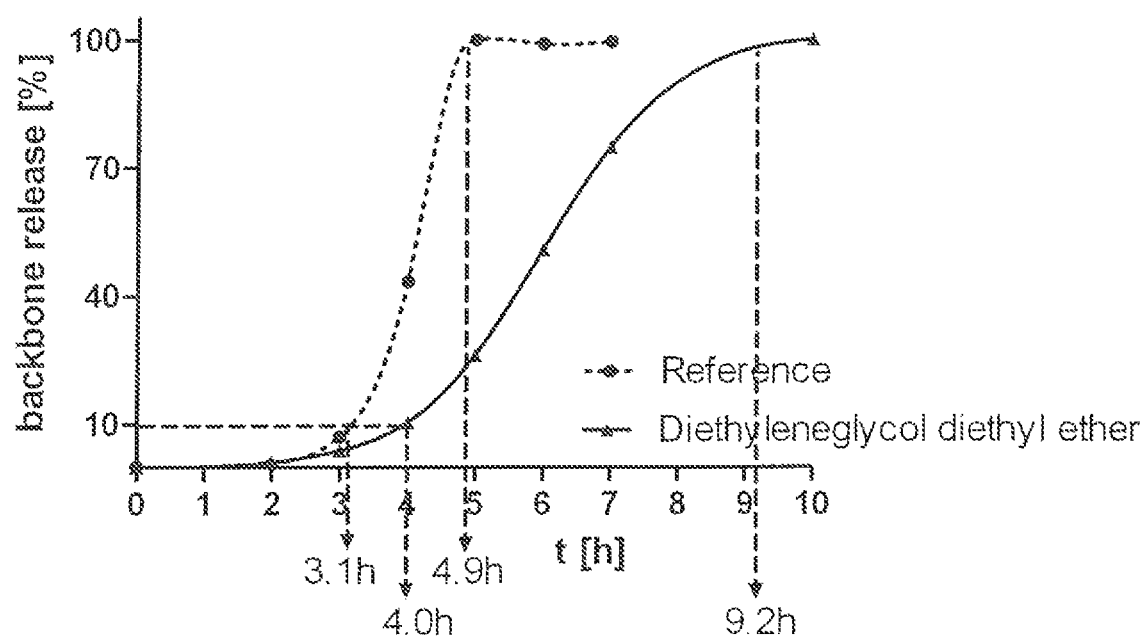
Figure 1C:
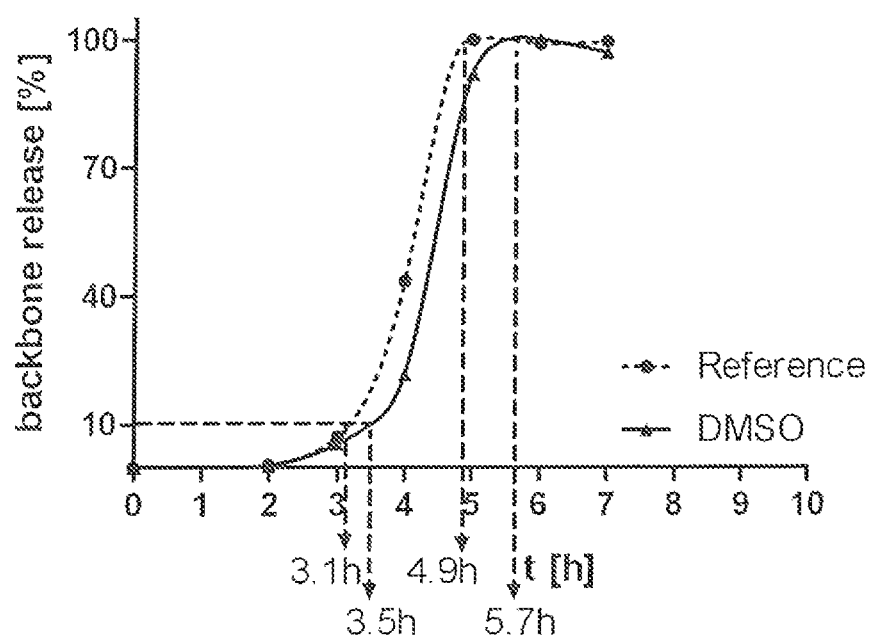
Figure 1D:
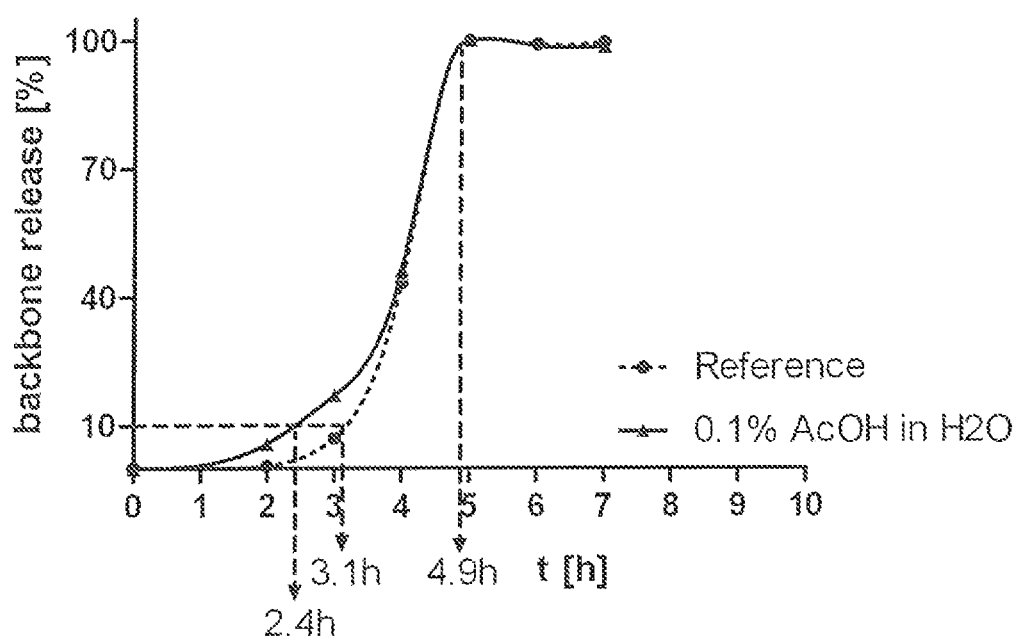
Figure 1E:
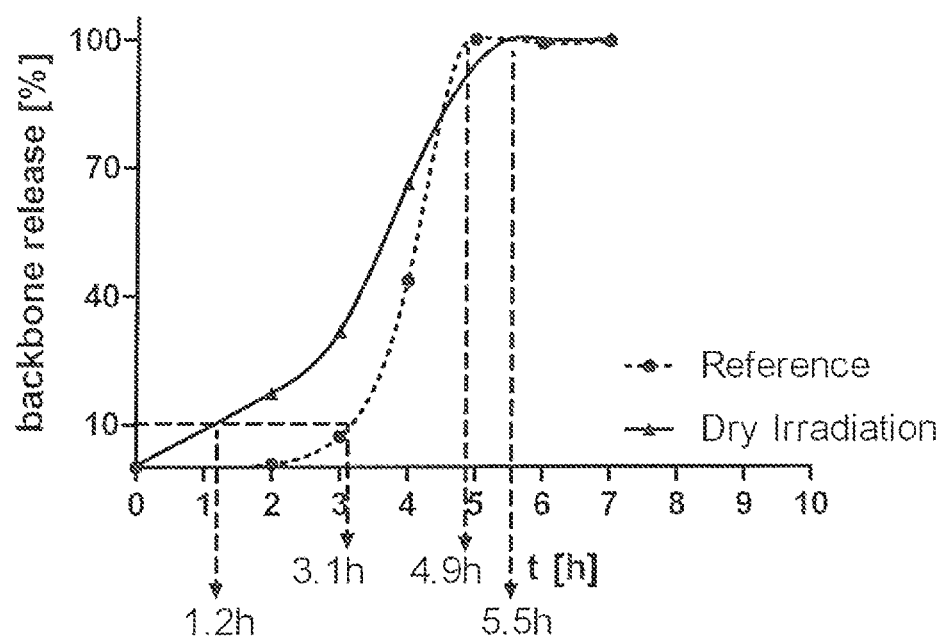
Figure 1F:
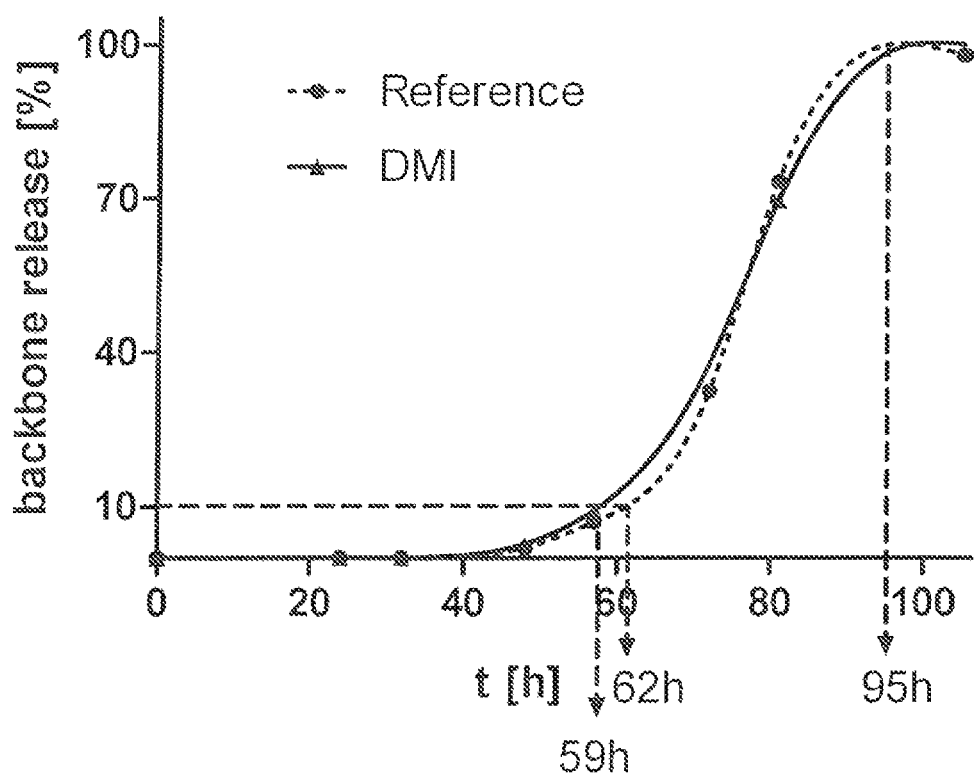
Figure 1G:
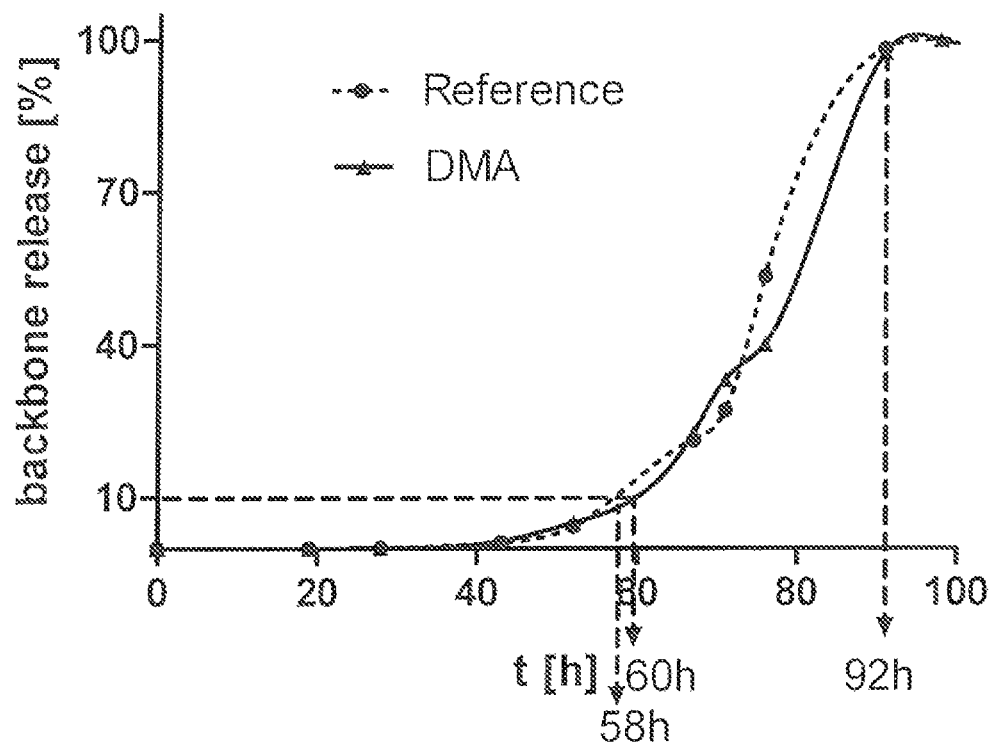
Figure 1H:
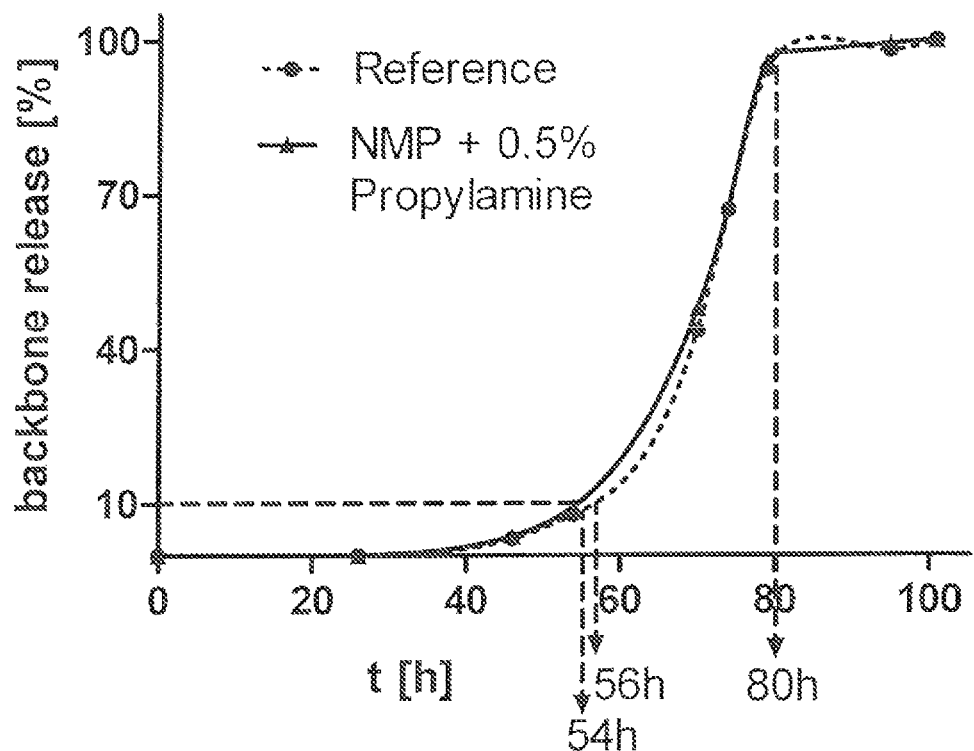
Figure 1I:
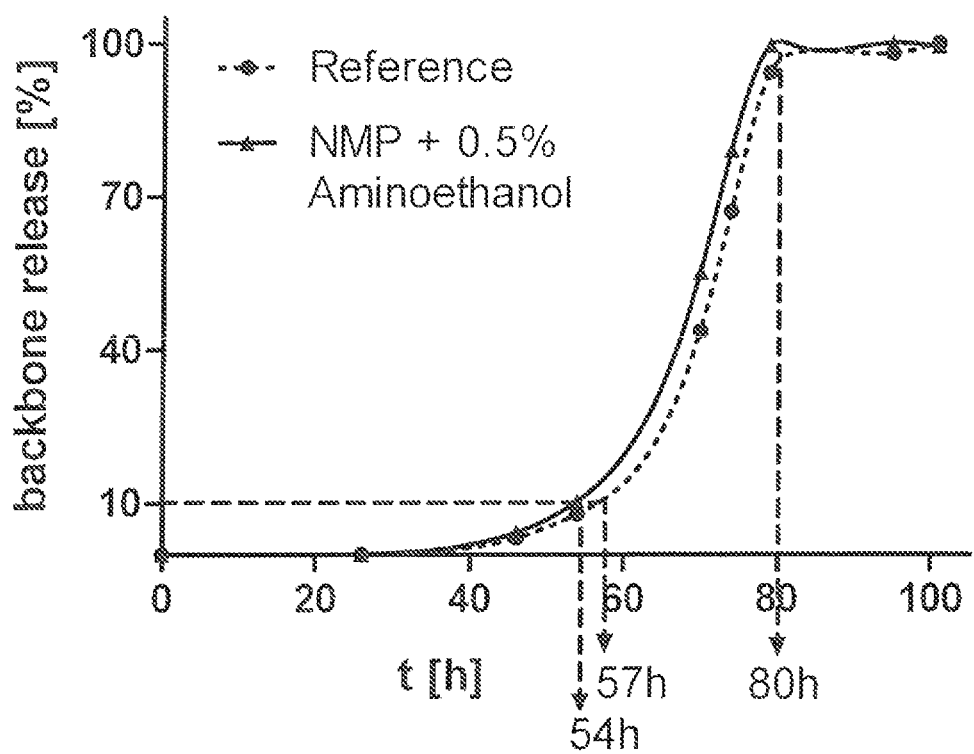
Figure 1J:
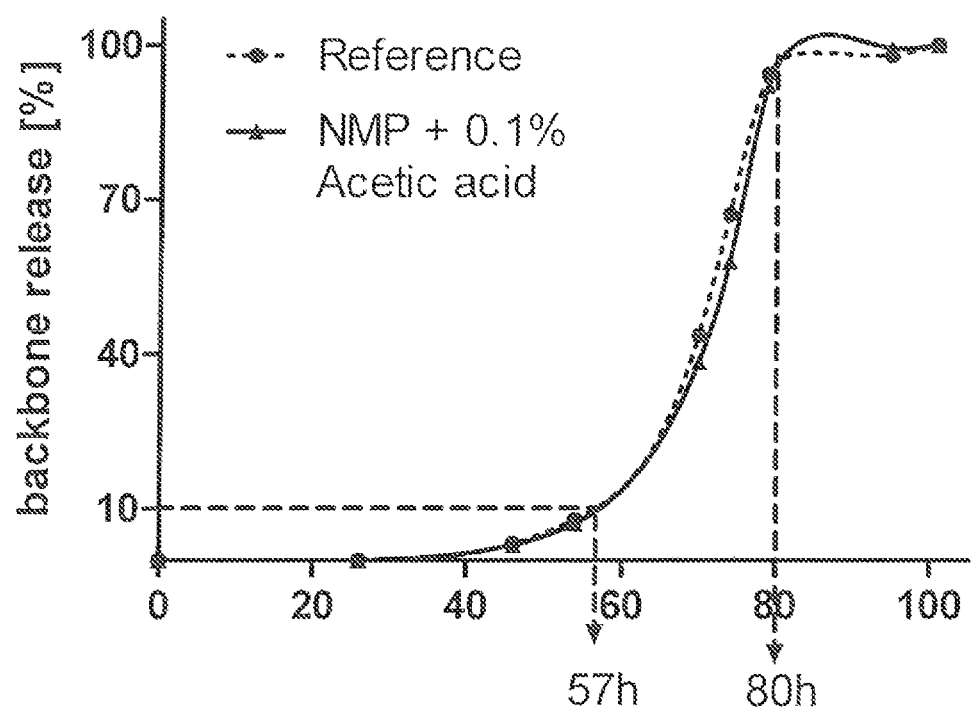
Figure 1K:
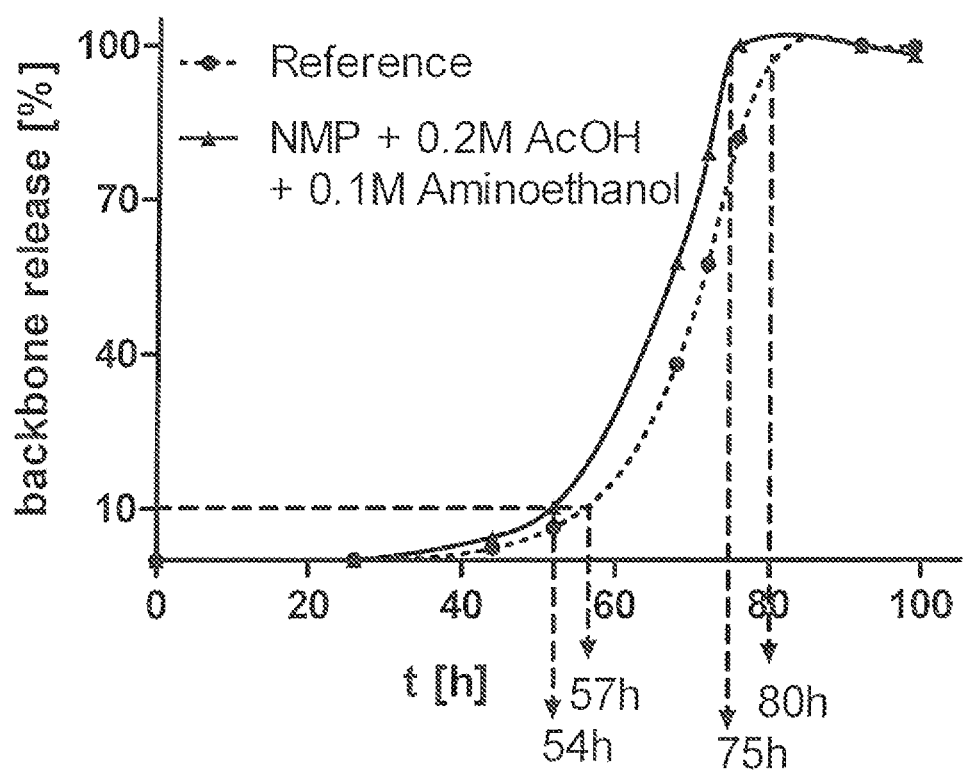

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The invention relates to a method to sterilize biodegradable PEG-based insoluble hydrogels through irradiation in the presence of a protective solvent which keeps the hydrogel intact. Biodegradable PEG-based insoluble hydrogels sterilized according to this invention have the same degradation kinetics and are fully degradable, meaning that no damage to the labile biodegradable bonds and thus also no damage to the stable bonds has occurred and no undesired crosslinking has happened, thus the intactness of the hydrogel is preserved. If a biodegradable PEG-based insoluble hydrogel sterilized according to the present invention contains reactive functional groups, the functionality of these groups is also preserved, i.e. the groups as such are preserved. Such reactive functional groups may serve as attachment points for direct or indirect linkage of an affinity ligand, chelating group, a drug, prodrug, carrier-linked prodrug or the like. Non-limiting examples of such reactive functional groups include, but are not limited to, carboxylic acid and activated derivatives, amino, maleimide, thiol, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, epoxide, oxirane, and aziridine; preferably carboxylic acid and activated derivatives, amino, thiol, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl arylating agents like aryl fluorides, hydroxylamine, disulfides like pyridyl disulfide, vinyl sulfone, vinyl ketone, oxirane, and aziridine. Preferred reactive functional groups include thiol, maleimide, amino, carboxylic acid and derivatives, carbonate and derivatives, carbamate and derivatives, aldehyde, and haloacetyl, more preferably thiol, amino, carboxylic acid and derivatives, carbonate and derivatives, carbamate and derivatives, aldehyde, and haloacetyl. Preferably, the reactive functional groups are primary amino groups or carboxylic acids, most preferred primary amino groups.

In one embodiment, the reactive functional groups of the biodegradable PEG-based insoluble hydrogel are protected with protecting groups, which are cleaved off after sterilization.

PEG-based insoluble hydrogels sterilized according to the present invention can be used in any application in which sterility is beneficial or required, such as, for example, tissue engineering, skin filling, intraocular devices, medical implants, surgical sealants and sponges, hemostatic agents, sustained release delivery systems, medical imaging agents and prodrug-carriers. The preferred use is as sustained release delivery systems and prodrug-carrier, most preferred as prodrug-carrier. The pre-formed three-dimensional hydrogel is sterilized by irradiation in the presence of a protective solvent or in a mixture of two or more protective solvents or aqueous solutions thereof and the sterile hydrogel can subsequently optionally be loaded with, for example, biologically active moieties, like for example peptides, proteins or small molecules. Such biologically active moieties can be linked to the hydrogel either via stable spacer moieties or through degradable linker moieties.

In an alternative embodiment, the biodegradable PEG-based insoluble hydrogel is first loaded with small molecule biologically active moieties and then sterilized by irradiation in the presence of a protective solvent or in a mixture of two or more protective solvents or aqueous solutions thereof.

A PEG-based insoluble hydrogel suitable for sterilization according to the present invention can be of various shapes and includes, but is not limited to, amorphous, spherical, lenticular, flat (such as in films) or tubular hydrogels. In a preferred embodiment, the PEG-based insoluble hydrogel consists of spherical microparticles with a particle diameter of 1 to 1000 microns, preferably 10 to 100 microns.

A PEG-based insoluble hydrogel suitable for sterilization according to the present invention is composed of backbone moieties interconnected by degradable bonds. Optionally, the backbone moieties may be crosslinked through oligomeric, polymeric or low-molecular weight crosslinking moieties, which are joined with the backbone through degradable bonds and may additionally carry degradable bonds. Optionally, backbone moieties may carry permanent linkages to one or more of the following: ligands, chelating groups, spacer molecules, blocking groups.

In one embodiment of the present invention the hydrogel has the following composition.

The biodegradable PEG-based insoluble hydrogel is composed of backbone moieties interconnected by hydrolytically degradable bonds. Preferably, the backbone moiety has a molecular weight in the range of from 1 kDa to 20 kDa, more preferably from 1 kDa to 15 kDa.

Preferably, in the biodegradable PEG-based insoluble hydrogel, a backbone moiety is characterized by a number of functional groups, consisting of interconnected biodegradable functional groups and reactive functional groups. Preferably, the sum of interconnected biodegradable groups and reactive functional groups is equal to or greater than 16, preferably 16-128, preferred 20-100, also preferred 20-40, more preferred 24-80, also more preferred 28-32 even more preferred 30-60; most preferred 30-32. It is understood that in addition to the interconnected functional groups and the reactive functional groups also protective groups may be present.

The functional groups may be attached to a linear chain. In this case, the functional groups may be spaced regularly or irregularly across the chain, or alternatively, the chain may be terminated by two dendritic moieties, providing for the total of functional groups.

Preferentially, a backbone moiety is characterized by having a branching core, from which at least three PEG-based polymeric chains extend. Such branching cores may comprise in bound form poly- or oligoalcohols, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may comprise in bound form poly- or oligoamines such as ornithine, diaminobutyric acid, trilysine, tetralysine, pentalysine, hexalysine, heptalysine, octalysine, nonalysine, decalysine, undecalysine, dodecalysine, tridecalysine, tetradecalysine, pentadecalysine or oligolysines, polyethyleneimines, polyvinylamines. Preferably, the branching core may comprise in bound form poly- or oligoamines such as trilysine, tetralysine, pentalysine, hexalysine, heptalysine, octalysine, nonalysine, decalysine, undecalysine, dodecalysine, tridecalysine, tetradecalysine, pentadecalysine or oligolysines, polyethyleneimines, polyvinylamines.

Preferably, the branching core extends three to sixteen PEG-based polymeric chains, more preferably four to eight.

The sum of interconnected functional groups and reactive functional groups of a backbone moiety is equally divided by the number of PEG-based polymeric chains extending from the branching core. If the number of PEG-based polymeric chains extending from the branching core does not allow for an equal distribution, it is preferred that the deviation from the mean number of the sum of interconnected functional groups and reactive functional groups per PEG-based polymeric chain is kept to a minimum.

More preferably, the sum of interconnected functional groups and reactive functional groups of a backbone moiety is equally divided by the number of PEG-based polymeric chains extending from the branching core. For instance, if there are 32 interconnected functional groups and reactive functional groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

Preferred structures for corresponding PEG-based polymeric chains extending from a branching core suitable for backbone moieties are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 2.5 kDa to 15 kDa and even more preferably 5 kDa to 10 kDa. It is understood that these reagents are present in the hydrogel in bound form.

Such additional functional groups may be provided by dendritic moieties.

Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties are trilysine, tetralysine, pentalysine, hexalysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine in bound form. Examples for such preferred dendritic moieties comprise trilysine, tetralysine, pentalysine, hexalysine, heptalysine, most preferred trilysine, pentalysine or heptalysine in bound form.

Most preferably, the biodegradable PEG-based insoluble hydrogel is characterized in that the backbone moiety has a quarternary carbon of formula $C(A\text{-}Hyp)_4$, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four functional groups representing the interconnected biodegradable functional groups and reactive functional groups and permanent bonds. Each backbone moiety contains at least 16 interconnected biodegradable functional groups and reactive functional groups and permanent bonds, preferably 20 to 64 and more preferably 28 to 64 interconnected biodegradable functional groups and reactive functional groups and permanent bonds.

Preferably, each A is independently selected from the formula —$(CH_2)_{n1}(OCH_2CH_2)_n X$—, wherein n1 is 1 or 2; n is an integer in the range of from 5 to 50; and X is a functional group covalently linking A and Hyp.

Preferably, A and Hyp are covalently linked by an amide functional group.

Preferably, the dendritic moiety Hyp is a hyperbranched polypeptide.

Preferably, the hyperbranched polypeptide is comprised of lysines in bound form, most preferably Hyp is undecalysinyl or heptalysinyl. Preferably, each dendritic moiety Hyp has a molecular weight in the range of from 0.4 kDa to 4 kDa. It is understood that a backbone moiety $C(A\text{-}Hyp)_4$ can consist of the same or different dendritic moieties Hyp and that each Hyp can be chosen independently. Each moiety Hyp consists of between 5 and 21 lysines, preferably of at least 7 lysines, i.e. each moiety Hyp is comprised of between 5 and 32 lysines in bound form, preferably of at least 7 lysines in bound form.

Preferably, C(A-Hyp)$_4$ has a molecular weight in the range of from 1 kDa to 20 kDa, more preferably 1 kDa to 15 kDa and even more preferably 1 kDa to 10 kDa.

Biodegradability of the hydrogels according to the present invention is achieved by introduction of hydrolytically degradable bonds.

Preferably, backbone moieties may be linked together through crosslinker moieties, each crosslinker moiety being terminated by at least two of the hydrolytically degradable bonds. In addition to the terminating degradable bonds, the crosslinker moieties may contain further biodegradable bonds. Thus, each end of the crosslinker moiety linked to a backbone moiety comprises a hydrolytically degradable bond, and additional biodegradable bonds may optionally be present in the crosslinker moiety.

Accordingly, the biodegradable PEG-based insoluble hydrogel comprises backbone moieties which are interconnected by hydrolytically degradable bonds and wherein the backbone moieties are preferably linked together through crosslinker moieties, each crosslinker moiety being terminated by at least two of the hydrolytically degradable bonds.

The biodegradable PEG-based insoluble hydrogel may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

The term biodegradable bond describes linkages that are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, carboxylic esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are carboxylic esters, carbonates, phosphoesters and sulfonic acid carboxylic esters and most preferred are carboxylic esters or carbonates.

Preferably, crosslinker moieties have a molecular weight in the range of from 60 Da to 5 kDa, more preferably, from 60 Da to 4 kDa, even more preferably from 60 Da to 3 kDa, even more preferably form 0.5 to 4 kDa, even more preferably from 1 kDa to 4 kDa and most preferably from 1 kDa to 3 kDa. In one embodiment, a crosslinker moiety consists of a polymer.

In addition to oligomeric or polymeric crosslinking moieties, low-molecular weight crosslinking moieties may be used, especially when hydrophilic high-molecular weight backbone moieties are used for the biodegradable PEG-based insoluble hydrogel formation.

Preferably, the poly(ethylene glycol) based crosslinker moieties are hydrocarbon chains comprising ethylene glycol units, optionally comprising further functional groups, wherein the poly(ethylene glycol) based crosslinker moieties comprise at least each m ethylene glycol units, wherein m is an integer in the range of from 3 to 100, preferably 1 to 70 and most preferably of from 10 to 70. Preferably, the poly(ethylene glycol) based crosslinker moieties have a molecular weight in the range of from 60 Da to 5 kDa and more preferably in the range of from 0.5 kDa to 5 kDa.

Preferably, the crosslinker moieties are PEG-based, preferably represented by only one PEG-based molecular chain. Preferably, the poly(ethylene glycol)-based crosslinker moieties are hydrocarbon chains comprising one or more ethylene glycol units, optionally comprising further chemical functional groups, wherein the poly(ethylene glycol) based crosslinker moieties comprise at least each m ethylene glycol units, wherein m is an integer in the range of from 1 to 100, preferably 3 to 100, preferably from 1 to 70 and even more preferably from 10 to 70. Preferably, the poly(ethylene glycol) based crosslinkers have a molecular weight from 60 Da to 5 kDa, preferably of from 0.5 kDa to 5 kDa.

In a preferred embodiment of the present invention the crosslinker moiety consists of a PEG chain, which is symmetrically connected through ester bonds to two alpha, omega-aliphatic dicarboxylic spacers provided by backbone moieties connected to the hyperbranched dendritic moiety through permanent amide bonds.

The dicarboxylic acids of the spacer moieties connected to a backbone moiety and on the other side is connected to a crosslinking moiety consists of 3 to 12 carbon atoms, most preferably between 5 and 8 carbon atoms and may be substituted at one or more carbon atom. Preferred substituents are alkyl groups, hydroxy groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

The hydrolysis rate of the biodegradable bonds between backbone moieties and crosslinker moieties is influenced or determined by the number and type of connected atoms adjacent to the PEG-ester carboxy group. For instance, by selecting from succinic, adipic or glutaric acid for PEG ester formation it is possible to vary the degradation half-lives of the biodegradable PEG-based insoluble hydrogel.

In an alternative embodiment, multi-functional moieties are coupled to the reactive functional groups of the polymerized hydrogel to increase the number of reactive functional groups which, for example, allows increasing the drug load of the biodegradable PEG-based insoluble hydrogel. Such multi-functional moieties may be provided by suitably substituted derivatives of lysine, dilysine, trilysine, tetralysine, pentalysine, hexalysine, heptalysine, or oligolysine, low-molecular weight PEI in bound form. Preferably, the multi-functional moiety is comprised of lysines in bound form. Optionally, such multi-functional moiety may be protected with protecting groups.

Further, such hydrogel according to the invention may be functionalized with a spacer carrying the same functional group, for instance, amino groups may be introduced into the hydrogel by coupling a heterobifunctional spacer, such as suitably activated COOH-PEG$_6$-NH-Fmoc, and removing the Fmoc-protecting group.

One preferred crosslinker moiety is shown below; dashed lines indicate interconnecting biodegradable linkages to backbone moieties:

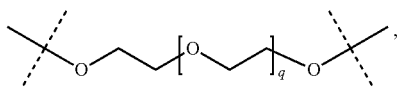

wherein q is an integer of from 5 to 50.

Preferably, the PEG-based insoluble hydrogel is composed of backbone moieties interconnected by hydrolytically degradable bonds.

More preferably, the backbone moieties comprise a branching core of the following formula:

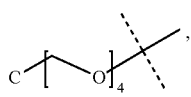

wherein the dashed line indicates attachment to the remainder of the backbone moiety.

More preferably, the backbone moieties comprise a structure of the following formula:

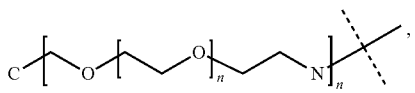

wherein n is an integer of from 5 to 50 and the dashed line indicates attachment to the remainder of the backbone moiety.

Preferably, backbone moiety comprises a hyperbranched moiety Hyp.

More preferably, the backbone moiety comprises a hyperbranched moiety Hyp of the following formula:

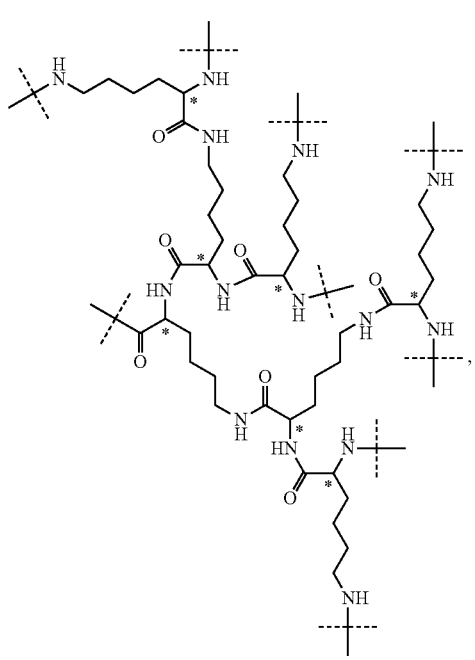

wherein the dashed lines indicate attachment to the rest of the molecule and carbon atoms marked with asterisks indicate in a preferred embodiment S-configuration. However, it is understood that hyperbranched moieties Hyp as shown above may also be in R-confirmation or may be racemic.

Preferably, the backbone moieties are attached to at least one spacer of the following formula:

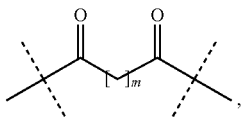

wherein one of the dashed lines indicates attachment to the hyperbranched moiety Hyp and the second dashed line indicates attachment to the rest of the molecule; and wherein m is an integer of from 2 to 4.

Preferably, the backbone moieties are linked together through crosslinker moieties having the following structure

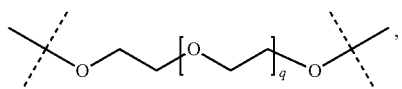

wherein q is an integer from 3 to 100.

More preferably, the backbone moieties of the PEG-based insoluble hydrogel are linked together through moieties of the following formula:

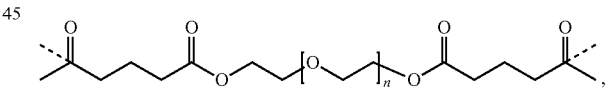

wherein each dashed line indicates attachment to a backbone moiety, respectively, and wherein n is 45.

Also more preferably the backbone moieties of the PEG-based insoluble hydrogel are linked together through moieties of the following formula:

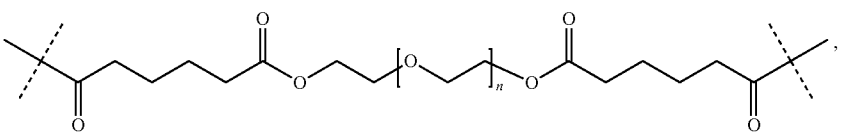

wherein the dashed lines indicate attachment to a backbone moiety, respectively, and wherein n is 22.

The present invention describes the sterilization of biodegradable PEG-based insoluble hydrogels through irradiation in the presence of protective solvents. The biodegradable PEG-based insoluble hydrogel used in this sterilization procedure is solvated with the protective solvent prior to irradiation and the protective solvent remains present during irradiation. Preferably, the protective solvent is selected from the group consisting of acetic acid (aqueous solution, 0.01-1% (v/v)), acetonitrile, 4-acetylmorpholine, dimethylsulfoxide (DMSO), dichloromethane (DCM), N,N-dimethylacetamide (DMA), N,N-dimethylformamide (DMF), 1,3-dimethyl-2-imidazolidinone (DMI), dimethylcarbonate, dimethylformamide, 1-ethyl-2-pyrrolidone, N-ethylacetamide, N-ethylformamide, formamide, 4-formylmorpholine, 1-formylpyrrolidone, 1,3-dimethyl-2-imidazolidinone, 1,3-Dimethyl-3,4,5,6-tetrahydro-2(1H)-pyrimidinone (DMPU), alkyl alcohols, like methanol, ethanol, propanol; formamide, hexamethylphosphoramide (HMPA), N-methylacetamide, nicotinamide (aqueous solution, 0.1-5% (w/w)), pyridoxine (aqueous solution, 0.1-5% (w/w)), N-methylformamide, NMP, 1,2-propylene carbonate, tetrahydrofuran (THF), sulfolan, water, or mixtures thereof.

More preferably, the protective solvent is selected from the group consisting of acetic acid (aqueous solution, 0.01-1% (v/v)), acetonitrile, dimethylsulfoxide (DMSO), dichloromethane (DCM), dimethylacetamid (DMA), dimethylcarbonate, dimethylformamide, 1,3-dimethyl-2-imidazolidinone, 1,3-dimethyl-3,4,5,6-tetrahydro-2(1H)-pyrimidinone (DMPU), alkyl alcohols, like methanol, ethanol, propanol; formamide, hexamethylphosphoramide (HMPA), nicotinamide (aqueous solution, 0.1-5% (w/w)), N-methylformamide, NMP, tetrahydrofuran (THF), sulfolan, water, or mixtures thereof.

Most preferably, the protective solvent is selected from 4-acetylmorpholine, DMA, DMF, DMI, DMPU, 1-ethyl-2-pyrrolidone, N-ethylacetamide, N-ethylformamide, 4-formylmorpholine, 1-formylpyrrolidone, N-methylacetamide, N-methylformamide, DMSO or NMP. Even more preferably the protective solvent is selected from DMSO, DMA, DMF, DMI or NMP; even more preferably DMA, DMF, DMI or NMP; also even more preferably DMSO or NMP, even more preferably NMP.

Optionally, the protective solvent is degassed and may optionally contain other, such as one or more protecting agents, such as salts, soluble in the protecting solvent. Preferably, the protective agent is comprised in a concentration ranging from 0.01 to 10%. It is understood that the protective solvent can also be a mixture of two or more protective solvents or aqueous dilutions thereof.

Protecting agents may be selected from the group consisting of optionally substituted linear, branched, or cyclical $C_1$-$C_{10}$ alkyl amines, optionally substituted linear or branched $C_1$-$C_{10}$ alkyl carboxylic acids, optionally substituted linear or branched $C_1$-$C_{10}$ alkyl sulfonic acids, optionally substituted linear or branched $C_1$-$C_{10}$ alkyl thiols, or carbohydrates. The protecting agents may be substituted with hydroxyl groups or substituted or interrupted with urea, amide, or carbamate groups or interrupted with ether. Mixtures of two or more protecting agents may be added to the protective solvent.

Preferred protecting agents are selected from propylamine, butylamine, pentylamine, sec. butylamine, ethanolamine, diethanolamine, serinol, trishydroxymethyl-aminomethane, acetic acid, formic acid, ascorbic acid, glycineamide, pivalic acid, propanoic acid, succinic acid, glutaric acid, adipic acid, thioglycerin, dithiothreitol, mercaptoethanol, reduced glutathione.

For sterilization, the biodegradable PEG-based insoluble hydrogel is placed in a suitable container, which ensures sterility after the sterilization procedure. Accordingly, the hydrogel is solvated with the protective solvent, and the suitable container is closed and subjected to the sterilization process. The suitable container is selected to ensure sterility after closing the container and performing the sterilization procedure. Alternatively, the PEG-based insoluble hydrogel is first solvated with the protective solvent and then transferred into the suitable container, in which it is sterilized, and the suitable container is then closed. Sterilization of the biodegradable PEG-based insoluble hydrogel is performed by irradiation, preferably with gamma-radiation, with a dose of 5-100 kGy, preferably 8-50 kGy, more preferably 20-40 kGy, such as for example 32-40 kGy and more preferably 20-30 kGy. Irradiation of the biodegradable PEG-based insoluble hydrogel according to the present invention may be performed at a temperature ranging from room temperature (25° C.) to −80° C. Preferably, irradiation is performed at room temperature. To obtain temperatures below room temperature, the suitable container comprising the biodegradable PEG-based insoluble hydrogel to be sterilized may be stored in a coolable environment or may be surrounded by a cooling substance, such as ice or dry ice.

Such sterilized biodegradable PEG-based insoluble hydrogel can either be used directly, for example as an implant, or can be further modified, for example by coupling biologically active moieties to the sterilized biodegradable PEG-based insoluble hydrogel. In the latter case, further processing is performed under sterile conditions, using pre-sterilized chemicals and biologically active moieties.

In one embodiment of the present invention, small molecule biologically active moieties are coupled to the functional groups of the biodegradable PEG-based insoluble hydrogel, resulting in a so called biodegradable PEG-based insoluble hydrogel carrying small molecule biologically active moieties, which is then sterilized by irradiation in the presence of a protective solvent. It is obvious to the person skilled in the art that only such small molecule biologically active moieties are suitable, that retain their chemical structure during gamma irradiation.

Accordingly, a preferred aspect of the present invention is a method according to the present invention, wherein the biodegradable PEG-based insoluble hydrogel is loaded with small molecule biologically active moieties.

If a biodegradable PEG-based insoluble hydrogel is loaded with small molecule biologically active moieties and sterilized by irradiation according to the present inventive method then the small molecule biologically active moiety should be preserved. The term "preserved" in this context preferably means that at least 90% of the small molecule biologically active moiety released from such sterilized hydrogel is unchanged, as can be measured by methods known to the person skilled in the art, such as by mass spectrometry, ultra performance liquid chromatography or pharmacological activity tests.

In a preferred embodiment of the present invention, dry biodegradable PEG-based insoluble hydrogel is solvated with 5-10 ml NMP/g dry biodegradable PEG-based insoluble hydrogel and irradiated with gamma rays with a dose of 25 kGy, using a closed container to prevent contaminations after sterilization. For further processing, like coupling of biologically active moieties to the sterilized hydrogel, NMP is exchanged for the desired solvent using syringes equipped with filters or suitable columns. It is obvious to the person skilled in the art that all steps after sterilization of the biodegradable PEG-based insoluble hydrogel are performed under aseptic conditions, using sterile solutions.

In an even more preferred embodiment of the present invention, per 1 g of dry biodegradable PEG-based insoluble hydrogel 5-10 ml NMP comprising 0.1%-2% (v/v) aminoethanol or propylamine are used to solvate the biodegradable PEG-based insoluble hydrogel and such solvated biodegradable PEG-based insoluble hydrogel is subsequently irradiated with gamma rays with a dose of 32 kGy, using a closed container to prevent contaminations after sterilization. For further processing, like coupling of biologically active moieties to the sterilized hydrogel, the NMP comprising 0.1%-2% (v/v) aminoethanol or propylamine is exchanged for the desired solvent using syringes equipped with filters or suitable columns. It is obvious to the person skilled in the art that all steps after sterilization of the biodegradable PEG-based insoluble hydrogel are performed under aseptic conditions, using sterile solutions.

A further aspect of the present invention is a sterilized biodegradable PEG-based insoluble hydrogel, especially loaded with small molecule biologically active moieties, obtainable by any of the methods of the present invention.

EXAMPLES

Materials and Methods

Materials

Amino 4-arm PEG5000 was obtained from JenKem Technology, Beijing, P. R. China).

All other chemicals were from Sigma-ALDRICH Chemie GmbH, Taufkirchen, Germany.

For hydrogel beads, syringes equipped with polypropylene frits were used as reaction vessels or for washing steps.

Analytics:

Electrospray ionization mass spectrometry (ESI-MS) was performed on a Thermo Fisher Orbitrap Discovery instrument equipped with Waters Acquity UPLC System.

MS spectra of PEG products showed a series of $(CH_2CH_2O)_n$ moieties due to polydispersity of PEG staring materials. For easier interpretation only one single representative m/z signal is given in the examples.

Size exclusion chromatography (SEC) was performed using an Amersham Bioscience AEKTAbasic system equipped with a Superdex75 5/150 GL column (Amersham Bioscience/GE Healthcare), if not stated otherwise. A 4/1 (v/v) aqueous buffer (20 mM sodium phosphate, 150 mM NaCl, 0.005% TWEEN 20, pH 7.4)/acetonitrile mixture was used as mobile phase. Absorption was detected at 215 nm.

Example 1

Synthesis of Backbone Reagent 1g

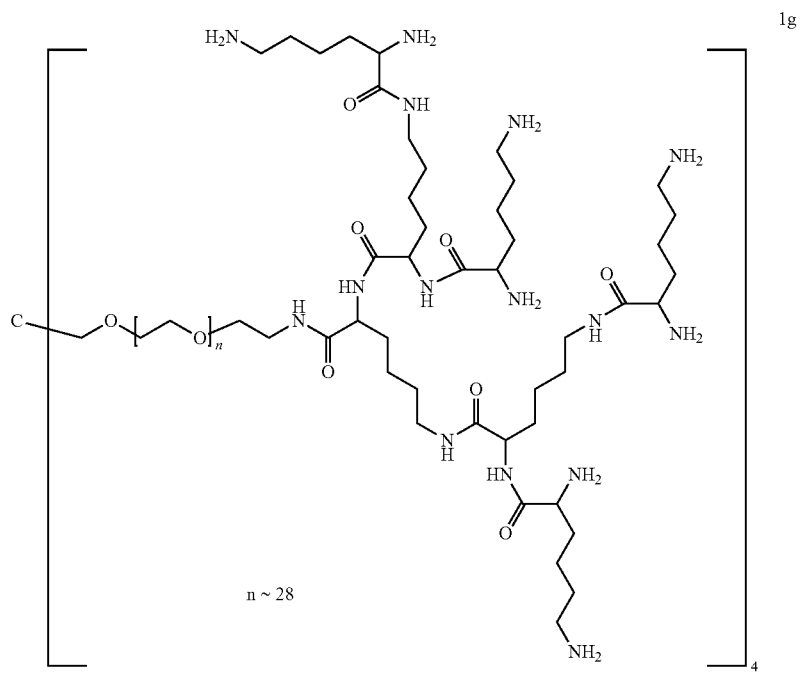

Backbone reagent 1g was synthesized from Amino 4-arm PEG5000 1a according to following scheme:

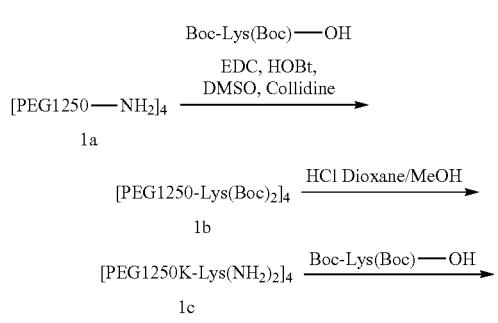

-continued

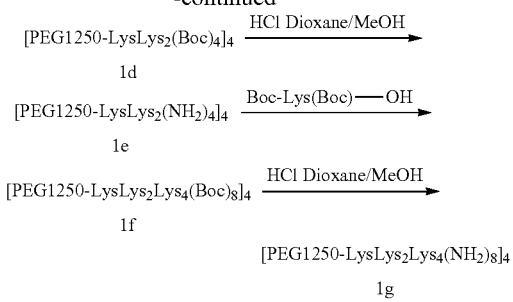

For synthesis of compound 1b, 4-Arm-PEG5000 tetraamine 1a (MW ca. 5200 g/mol, 5.20 g, 1.00 mmol, HCl salt) was dissolved in 20 mL of DMSO (anhydrous). Boc-Lys (Boc)-OH (2.17 g, 6.25 mmol) in 5 mL of DMSO (anhydrous), EDC HCl (1.15 g, 6.00 mmol), HOBt.H$_2$O (0.96 g, 6.25 mmol), and collidine (5.20 mL, 40 mmol) were added. The reaction mixture was stirred for 30 min at RT.

The reaction mixture was diluted with 1200 mL of dichloromethane and washed with 600 mL of 0.1 N H$_2$SO$_4$ (2×), brine (1×), 0.1 M NaOH (2×), and 1/1 (v/v) brine/water (4×). Aqueous layers were reextracted with 500 mL of DCM. Organic phases were dried over Na$_2$SO$_4$, filtered and evaporated to give 6.3 g of crude product 1b as colorless oil. Compound 1b was purified by RP-HPLC.

Yield 3.85 g (59%) colorless glassy product 1b.
MS: m/z 1294.4=[M+5H]$^{5+}$ (calculated=1294.6).

Compound 1c was obtained by stirring of 3.40 g of compound 1b (0.521 mmol) in 5 mL of methanol and 9 mL of 4 N HCl in dioxane at RT for 15 min. Volatiles were removed in vacuo. The product was used in the the next step without further purification.
MS: m/z 1151.9=[M+5H]$^{5+}$ (calculated=1152.0).

For synthesis of compound 1d, 3.26 g of compound 1c (0.54 mmol) were dissolved in 15 mL of DMSO (anhydrous). 2.99 g Boc-Lys(Boc)-OH (8.64 mmol) in 15 mL DMSO (anhydrous), 1.55 g EDC HCl (8.1 mmol), 1.24 g HOBt.H$_2$O (8.1 mmol), and 5.62 mL of collidine (43 mmol) were added. The reaction mixture was stirred for 30 min at RT.

Reaction mixture was diluted with 800 mL DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried with Na$_2$SO$_4$, filtered and evaporated to give a glassy crude product.

Product was dissolved in DCM and precipitated with cooled (−18° C.) diethylether. This procedure was repeated twice and the precipitate was dried in vacuo.
Yield: 4.01 g (89%) colorless glassy product 1d, which was used in the next step without further purification.
MS: m/z 1405.4=[M+6H]$^{6+}$ (calculated=1405.4).

Compound 1e was obtained by stirring a solution of compound 1d (3.96 g, 0.47 mmol) in 7 mL of methanol and 20 mL of 4 N HCl in dioxane at RT for 15 min. Volatiles were removed in vacuo. The product was used in the the next step without further purification.
MS: m/z 969.6=[M+7H]$^{7+}$ (calculated=969.7).

For the synthesis of compound 1f, compound 1e (3.55 g, 0.48 mmol) was dissolved in 20 mL of DMSO (anhydrous). Boc-Lys(Boc)-OH (5.32 g, 15.4 mmol) in 18.8 mL of DMSO (anhydrous), EDC HCl (2.76 g, 14.4 mmol), HOBt.H$_2$O (2.20 g, 14.4 mmol), and 10.0 mL of collidine (76.8 mmol) were added. The reaction mixture was stirred for 60 min at RT.

The reaction mixture was diluted with 800 mL of DCM and washed with 400 mL of 0.1 N H$_2$SO$_4$ (2×), brine (1×), 0.1 M NaOH (2×), and 1/1 (v/v) brine/water (4×). Aqueous layers were reextracted with 800 mL of DCM. Organic phases were dried over Na$_2$SO$_4$, filtered and evaporated to give crude product 1f as colorless oil.

Product was dissolved in DCM and precipitated with cooled (−18° C.) diethylether. This step was repeated twice and the precipitate was dried in vacuo.
Yield 4.72 g (82%) colourless glassy product 1f which was used in the next step without further purification.
MS: m/z 1505.3=[M+8H]$^{8+}$ (calculated=1505.4).

Backbone reagent 1g was obtained by stirring a solution of compound 1f (MW ca 12035 g/mol, 4.72 g, 0.39 mmol) in 20 mL of methanol and 40 mL of 4 N HCl in dioxane at RT for 30 min. Volatiles were removed in vacuo.
Yield 3.91 g (100%), glassy product backbone reagent 1g.
MS: m/z 977.2=[M+9H]$^{9+}$ (calculated=977.4).

Alternative Synthetic Route for 1g
For synthesis of compound 1b, to a 45° C. suspension of 4-Arm-PEG5000 tetraamine (1a) (50.0 g, 10.0 mmol) in 250 mL of iPrOH (anhydrous), boc-Lys(boc)-OSu (26.6 g, 60.0 mmol) and DIEA (20.9 mL, 120 mmol) were added and the mixture was stirred for 30 min.

Subsequently, n-propylamine (2.48 mL, 30.0 mmol) was added. After 5 min the solution was diluted with 1000 mL of MTBE and stored overnight at −20° C. without stirring. Approximately 500 mL of the supernatant were decanted off and discarded. 300 mL of cold MTBE were added and after 1 min shaking the product was collected by filtration through a glass filter and washed with 500 mL of cold MTBE. The product was dried in vacuo for 16 h.
Yield: 65.6 g (74%) 1b as a white lumpy solid
MS: m/z=937.4=[M+7H]$^{7+}$ (calculated=937.6).

Compound 1c was obtained by stirring of compound 1b from the previous step (48.8 g, 7.44 mmol) in 156 mL of 2-propanol at 40° C. A mixture of 196 mL of 2-propanol and 78.3 mL of acetylchloride was added under stirring within 1-2 min. The solution was stirred at 40° C. for 30 min and cooled to −30° C. overnight without stirring. 100 mL of cold MTBE were added, the suspension was shaken for 1 min and cooled for 1 h at −30° C. The product was collected by filtration through a glass filter and washed with 200 mL of cold MTBE. The product was dried in vacuo for 16 h.
Yield: 38.9 g (86%) 1c as a white powder
MS: m/z=960.1 [M+6H]$^{6+}$ (calculated=960.2).

For synthesis of compound 1d, to a 45° C. suspension of 1c from the previous step (19.0 g, 3.14 mmol) in 80 mL 2-propanol were added boc-Lys(boc)-OSu (16.7 g, 37.7 mmol) and DIEA (13.1 mL, 75.4 mmol) and the mixture was stirred for 30 min at 45° C. Subsequently, n-propylamine (1.56 mL, 18.9 mmol) was added. After 5 min the solution was precipitated with 600 mL of cold MTBE and centrifugated (3000 min$^{-1}$, 1 min) The precipitate was dried in vacuo for 1 h and dissolved in 400 mL THF 200 mL of diethyl ether were added and the product was cooled to −30° C. for 16 h without stirring. The suspension was filtered through a glass filter and washed with 300 mL cold MTBE. The product was dried in vacuo for 16 h.
Yield: 21.0 g (80%) 1d as a white powder
MS: m/z 1405.4=[M+6H]$^{6+}$ (calculated=1405.4).

Compound 1e was obtained by dissolving compound 1d from the previous step (15.6 g, 1.86 mmol) in 3 N HCl in methanol (81 mL, 243 mmol) and stirring for 90 min at 40° C. 200 mL of MeOH and 700 mL of iPrOH were added and the mixture was stored for 2 h at −30° C. For completeness of crystallization, 100 mL of MTBE were added and the suspension was stored at −30° C. overnight. 250 mL of cold MTBE were added, the suspension was shaken for 1 min and filtered through a glass filter and washed with 100 mL of cold MTBE. The product was dried in vacuo.

Yield: 13.2 g (96%) 1e as a white powder
MS: m/z=679.1=[M+10H]$^{10+}$ (calculated=679.1).

For the synthesis of compound 1f, to a 45° C. suspension of 1e from the previous step, (8.22 g, 1.12 mmol) in 165 mL 2-propanol were added boc-Lys(boc)-OSu (11.9 g, 26.8 mmol) and DIEA (9.34 mL, 53.6 mmol) and the mixture was stirred for 30 min. Subsequently, n-propylamine (1.47 mL, 17.9 mmol) was added. After 5 min the solution was cooled to −18° C. for 2 h, then 165 mL of cold MTBE were added, the suspension was shaken for 1 min and filtered through a glass filter. Subsequently, the filter cake was washed with 4×200 mL of cold MTBE/iPrOH 4:1 and 1×200 mL of cold MTBE. The product was dried in vacuo for 16 h.

Yield: 12.8 g, MW (90%) 1f as a pale yellow lumpy solid
MS: m/z 1505.3=[M+8H]$^{8+}$ (calculated=1505.4).

Backbone reagent 1g was obtained by dissolving 4Arm-PEG5 kDa(-LysLys$_2$Lys$_4$(boc)$_8$)$_4$ (1f) (15.5 g, 1.29 mmol) in 30 mL of MeOH and cooling to 0° C. 4 N HCl in dioxane (120 mL, 480 mmol, cooled to 0° C.) was added within 3 min and the ice bath was removed. After 20 min, 3 N HCl in methanol (200 mL, 600 mmol, cooled to 0° C.) was added within 15 min and the solution was stirred for 10 min at room temperature. The product solution was precipitated with 480 mL of cold MTBE and centrifugated at 3000 rpm for 1 min. The precipitate was dried in vacuo for 1 h and redissolved in 90 mL of MeOH, precipitated with 240 mL of cold MTBE and the suspension was centrifugated at 3000 rpm for 1 min again. The product was dried in vacuo Yield: 11.5 g (89%) as pale yellow flakes.
MS: m/z=1104.9 [M+8H]$^{8+}$ (calculated=1104.9).

Example 2

Synthesis of Crosslinker Reagents 2d

Crosslinker reagent 2d was prepared from adipic acid mono benzyl ester (English, Arthur R. et al., *Journal of Medicinal Chemistry*, 1990, 33(1), 344-347) and PEG2000 according to the following scheme:

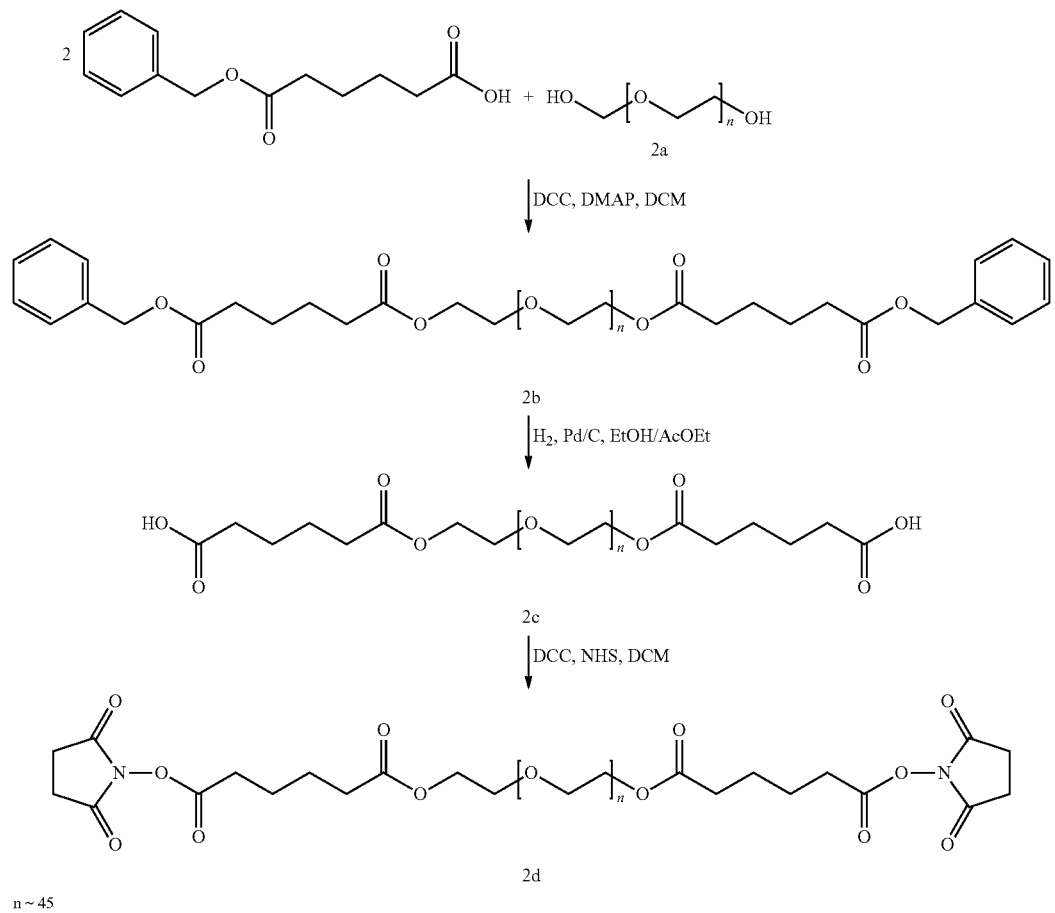

A solution of PEG2000 (2a) (11.0 g, 5.5 mmol) and benzyl adipate half-ester (4.8 g, 20.6 mmol) in dichloromethane (90.0 mL) was cooled to 0° C. Dicyclohexylcarbodiimide (4.47 g, 21.7 mmol) was added followed by a catalytic amount of DMAP (5 mg) and the solution was stirred and allowed to reach room temperature overnight (12 h). The flask was stored at +4° C. for 5 h. The solid was filtered and the solvent completely removed by destillation in vacuo. The residue was dissolved in 1000 mL 1/1(v/v) ether/ethyl acetate and stored at RT for 2 hours while a small amount of a flaky solid was formed. The solid was removed by filtration through a pad of Celite®. The solution was stored in a tightly closed flask at −30° C. in the freezer for 12 h until crystallisation was complete. The crystalline product was filtered through a glass frit and washed with cooled ether (−30° C.). The filter cake was dried in vacuo. Yield: 11.6 g (86%) 2b as a colorless solid. The product was used without further purification in the next step.

MS: m/z 813.1=$[M+3H]^{3+}$ (calculated=813.3)

In a 500 mL glass autoclave PEG2000-bis-adipic acid-bis-benzyl ester 2b (13.3 g, 5.5 mmol) was dissolved in ethyl acetate (180 mL) and 10% Palladium on charcoal (0.4 g) was added. The solution was hydrogenated at 6 bar, 40° C. until consumption of hydrogen had ceased (5-12 h). Catalyst was removed by filtration through a pad of Celite® and the solvent was evaporated in vacuo. Yield: 12.3 g (quantitative) 2c as yellowish oil. The product was used without further purification in the next step.

MS: m/z 753.1=$[M+3H]^{3+}$ (calculated=753.2)

A solution of PEG2000-bis-adipic acid half ester 2c (9.43 g, 4.18 mmol), N-hydroxysuccinimide (1.92 g, 16.7 mmol) and dicyclohexylcarbodiimide (3.44 g, 16.7 mmol) in 75 mL of DCM (anhydrous) was stirred over night at room temperature. The reaction mixture was cooled to 0° C. and precipitate was filtered off. DCM was evaporated and the residue was recystallized from THF.

Yield: 8.73 g (85%) crosslinker reagent 2d as colorless solid.

MS: m/z 817.8=$[M+3H]^{3+}$ (calculated=817.9).

Example 3

Preparation of Low Density Hydrogel Beads Containing Free Amino Groups 3a

A solution of 300 mg 1g and 900 mg 2d in 10.80 mL DMSO was added to a solution of 100 mg Arlacel P135 (Croda International Plc) in 80 mL heptane. The mixture was stirred at 700 rpm with a custom metal stirrer for 10 min at RT to form a suspension. 1.1 mL N,N,N',N'-tertramethylene diamine (TMEDA) was added to effect polymerization. After 2 h, the stirrer speed was reduced to 400 rpm and the mixture was stirred for additional 16 h. 1.6 mL of acetic acid were added and then after 10 min 50 mL of water were added. After 5 min, the stirrer was stopped and the aqueous phase was drained.

For bead size fractionation, the water-hydrogel suspension was wet-sieved on 75, 50, 40, 32 and 20 μm steel sieves. Bead fractions that were retained on the 32, 40, and 50 μm sieves were pooled and washed 3 times with water, 10 times with ethanol and dried for 16 h at 0.1 mbar to give 3a as a white powder.

Preparation of Medium Density Hydrogel Beads Containing Free Amino Groups 3b

A solution of 1200 mg 1g and 3840 mg 2d in 28.6 mL DMSO was added to a solution of 425 mg Arlacel P135 (Croda International Plc) in 100 mL heptane. The mixture was stirred at 650 rpm with a custom metal stirrer for 10 min at RT to form a suspension. 4.3 mL N,N,N',N'-tertramethylene diamine (TMEDA) was added to effect polymerization. After 2 h, the stirrer speed was reduced to 400 rpm and the mixture was stirred for additional 16 h. 6.6 mL of acetic acid were added and then after 10 min 50 mL of water were added. After 5 min, the stirrer was stopped and the aqueous phase was drained.

For bead size fractionation, the water-hydrogel suspension was wet-sieved on 63, 50, 40, 32 and 20 μm steel sieves. Bead fractions that were retained on the 32, 40, and 50 μm sieves were pooled and washed 3 times with water, 10 times with ethanol and dried for 16 h at 0.1 mbar to give 2.86 g of 3b as a white powder.

Preparation of High Density Hydrogel Beads Containing Free Amino Groups 3c

A solution of 2400 mg 1g and 3600 mg 2d in 24.0 mL DMSO was added to a solution of 425 mg Arlacel P135 (Croda International Plc) in 110 mL heptane. The mixture was stirred at 850 rpm with a custom metal stirrer for 10 min at RT to form a suspension. 8.6 mL N,N,N',N'-tertramethylene diamine (TMEDA) was added to effect polymerization. After 2 h, the stirrer speed was reduced to 400 rpm and the mixture was stirred for additional 16 h. 13.2 mL of acetic acid were added and then after 10 min 50 mL of water were added. After 5 min, the stirrer was stopped and the aqueous phase was drained.

For bead size fractionation, the water-hydrogel suspension was wet-sieved on 63, 50, 40, 32 and 20 μm steel sieves. Bead fractions that were retained on the 32, 40, and 50 μm sieves were pooled and washed 3 times with water, 10 times with ethanol and dried for 16 h at 0.1 mbar to give 3.00 g of 3c as a white powder.

Example 4

Preparation and subsequent gamma irradiation of hydrogel beads (4a, 4b, 4c, 4d, 4e, 4f, 4g, 4h, 4i, 4j, 4k)

20 mg portions of the dried hydrogel 3a in syringes equipped with a filter were washed five times with the following protective solvents: NMP (4a), diethylene glycol diethyl ether (DGDE) (4b), DMSO (4c), or 0.1% acetic acid in water (4d).

Likewise 20 mg portions of the dried hydrogel 3b in syringes equipped with a filter were washed five times with the following protective solvents: DMI (4f), DMA (4g), NMP+0.5 vol 1-propylamine (4h), NMP+0.5 vol % 2-aminoethanol (ethanolamine) (4i), NMP+0.1 vol acetic acid (4j), or NMP containing 0.2 M AcOH and 0.1 M propylamine (4k).

After the last washing, the syringes were closed, leaving the hydrogel beads in a swollen form with a little excess of protective solvent.

Additionally a dried sample of hydrogel 3a was irradiated in the dry state to give 4e.

Samples were gamma-irradiated at room temperature with a dose of 40 kGy (4a, 4b, 4c, 4d, 4e, 4f) or 32 kGy (4g, 4h, 4i, 4j, 4k) (irradiation source: Co 60). Subsequently, the samples were washed five times with ethanol and dried for 16 h at 0.1 mbar.

Example 5

Determination of Amino Content

Fmoc-Asp(OtBu)-OSu (49 mg, 116 μmol) was dissolved in 0.9 mL acetonitrile, and 0.5 mL 50 mM sodium phosphate buffer, pH 7.4 was added. The solution was added to 20 mg hydrogel 3a and 4a in a syringe reactor and shaken for 30 min at ambient temperature.

Subsequently, the hydrogel was washed 10× with acetonitrile/water 2:1 (v/v)+0.1% TFA and 10× with DMF.

The Fmoc-group was cleaved by shaking 3×10 min with DMF/DBU 98/2 (v/v) and washing 10× with DMF/DBU 98/2

(v/v). All these fractions were pooled, diluted with DMF and the amount of 9-methylene fluorene was determined by measuring UV absorption at 295 nm. An extinction coefficient of 9141 L mol$^{-1}$ cm$^{-1}$ was used.

Amino loading of 3a: 0.13 mmol/g

Amino loading of 4a after gamma-irradiation: 0.12 mmol/g

Alternative use of Fmoc-Gly-OSu instead of Fmoc-Asp(OtBu)-OSu results in the same amino loading values.

Example 6

Accelerated in Vitro Degradation Analysis of Hydrogel Beads

In vitro degradation kinetics of hydrogel beads 4a, 4b, 4c, 4d, 4e, 4f, 4g, 4h, 4i, 4j and 4k after sterilization and 3a and 3b (reference material, no sterilization) under accelerated conditions were measured by incubating 5 mg of each sample in 0.5 mL 0.5 M sodium carbonate buffer, pH 10.3 at 37° C. (3a, 4a, 4b, 4c, 4d and 4e). Alternatively 0.5 mL 0.5 M sodium borate buffer pH 9.0 at 37° C. conditions were used for accelerated in vitro degradation (3b, 4f, 4g, 4h, 4i, 4j and 4k). Aliquots were taken at time intervals and analyzed by SEC. UV-signals corresponding to released water-soluble degradation products of the hydrogel, comprising one or more backbone moieties, were integrated and plotted against incubation time (FIG. 1).

irradiated in a bed of dry ice with a dose of 40 kGy (irradiation source: Co 60). Subsequently, hydrogel 6 was washed five times with formulation buffer, five times with water and five times with ethanol and dried for 16 h at 0.1 mbar.

Example 8

In Vitro Degradation of Irradiated 6 at pH 9 and 37° C.

Figure 2:
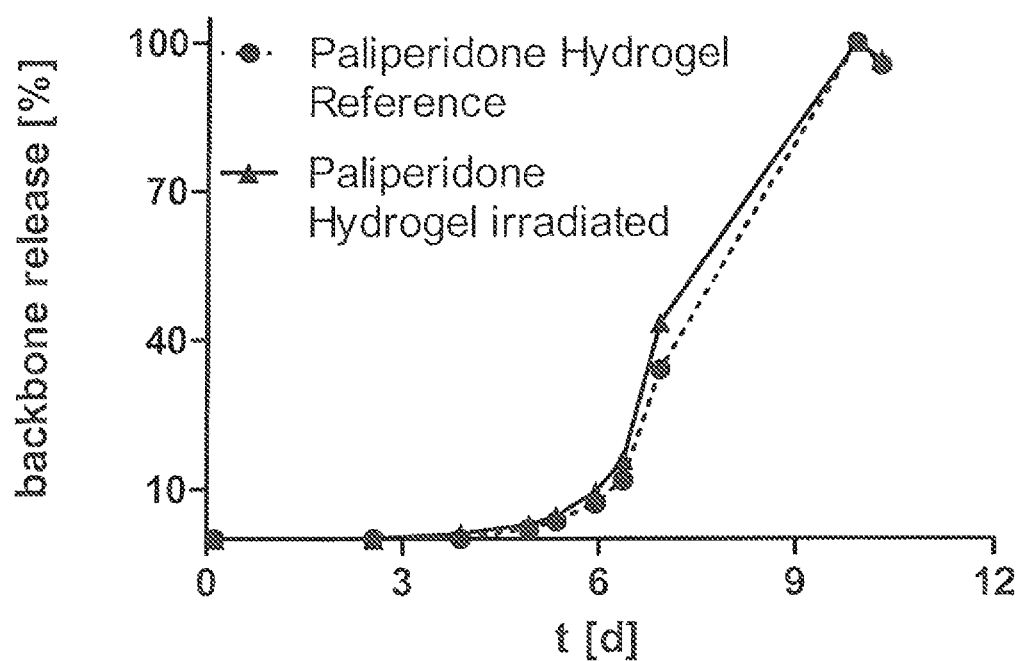
FIG. 2 shows the in vitro degradation kinetics of 6 after sterilization together with 5 (unsterilized hydrogel, "reference"), at pH 9.0, 37° C.

In vitro degradation kinetics of hydrogel 6 (after sterilization) and reference 5 (no sterilization) under accelerated conditions was measured by incubating 2 mg of each sample in 1.0 mL 0.5 M sodium borate buffer pH 9.0 at 37° C. Aliquots were taken at time intervals and analyzed by SEC. UV-signals (215 nm) corresponding to released water-soluble degradation products of the hydrogel, comprising one or more backbone moieties, were integrated and plotted against incubation time. Only small deviations in degradation behaviour were observed (FIG. 2).

Example 9

Quality of Released Paliperidone from Irradiated Hydrogel 6

1 mg irradiated paliperdione-linker-hydrogel 6 was incubated in 1.5 mL pH 7.4 phosphate buffer (60 mM, 3 mM

| Sample | Solvent | Time for the release of the first 10% of backbone moieties (a) | Time for the release of 95% of backbone moieties (b) | Ratio a/b | Fig. |
|---|---|---|---|---|---|
| 3a (pH 10.3) | | 3.1 h | 4.9 h | 1.58 | 1a |
| 4a | NMP | 3.1 h | 4.9 h | 1.58 | 1a |
| 4b | DGDE | 4.0 h | 9.2 h | 2.25 | 1b |
| 4c | DMSO | 3.5 h | 5.7 h | 1.63 | 1c |
| 4d | 0.1 % AcOH | 2.4 h | 4.9 h | 2.04 | 1d |
| 4e | none | 1.2 h | 5.5 h | 4.58 | 1e |
| 3b (pH 9.0) | | 62 h | 95 h | 1.53 | 1f |
| 4f | DMI | 59 h | 95 h | 1.61 | 1f |
| 4g | DMA | 60 h | 92 h | 1.53 | 1g |
| 4h | NMP 0.5% propylamine | 54 h | 80 h | 1.48 | 1h |
| 4i | NMP 0.5% aminoethanol | 54 h | 80 h | 1.48 | 1i |
| 4j | NMP 0.1% AcOH | 57 h | 80 h | 1.40 | 1j |
| 4k | NMP 0.1M AcOH, 0.2M propylamine | 54 h | 75 h | 1.39 | 1k |

Example 7

Preparation of Gamma Irradiated Paliperidone Loaded Hydrogel 6

Paliperidone loaded hydrogel 5 was prepared by hydrogel 3c modification with lysine and subsequent paliperidone-glutaryl ester coupling as described in international patent application PC/EP2010/064874. A 20 mg portion of the dried hydrogel beads 5 in a syringe equipped with a filter was washed five times with formulation buffer (85 g/l trehalose dihydrate, 50 mM succinate/Tris buffer pH 5.0, 0.05% Tween 20, 1 mM EDTA). After the last washing step, the syringe was closed, leaving the hydrogel beads in a swollen form with a little excess of protective solvent. The sample was gamma- EDTA, 0.01% Tween-20) at 37° C. After 4 d the quality of paliperidone released in the supernatant was checked by HPLC A Waters Acquity UPLC was used equipped with a Waters BEH C18 column, 50×2.1 mm I.D., 1.7 μm particle size. Solvent A: 0.05% TFA in water, solvent B: 0.04% TFA in acetonitrile. A linear gradient from 0-50% B in 4 min was employed. A paliperidone purity of 95% was found (215 nm).

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

Abbreviations
AcOEt ethyl acetate
AcOH acetic acid
Asp aspartic acid
Boc t-butyloxycarbonyl
DBU 1,8-Diazabicyclo[5.4.0]undec-7-en
DCC dicyclohexylcarbodiimide
DCM dichloromethane
DGDE diethylene glycol diethyl ether
DMA N,N-dimethylacetamide
DMAP dimethylamino-pyridine
DMF N,N-dimethylformamide
DMI 1,3-dimethyl-2-imidazolidinone
DMSO dimethylsulfoxide
EDC 1-Ethyl-3-(3-dimethylaminopropyl)carbodiimide
ESI electrospray ionization
eq stoichiometric equivalent
EtOH ethanol
Fmoc fluorenylmethoxycarbonyl
HOBt N-hydroxybenzotriazole
iPrOH isopropanol
kGy kilogray
LCMS mass spectrometry-coupled liquid chromatography
MeOH methanol
MS mass spectrum
MTBE methyl tert.-butyl ether
MW molecular mass
NHS N-hydroxy succinimide
NMP N-methyl-2-pyrrolidinone
OtBu tert.-butyloxy
OSu N-hydroxy succinimidyl
PEG poly(ethylene glycol)
PyBOP benzotriazole-1-yl-oxy-tris-pyrrolidino-phosphonium hexafluorophosphate
RP-HPLC reversed-phase high performance liquid chromatography
RT room temperature
SEC size exclusion chromatography
tBu tert.-butyl
TFA trifluoroacetic acid
THF tetrahydrofurane
TMEDA N,N,N',N'-tertramethylene diamine
UV ultraviolet
VIS visual

The invention claimed is:

1. A sterilized biodegradable poly(ethylene glycol) based insoluble hydrogel comprising:
   backbone moieties which are interconnected by hydrolytically degradable bonds;
   wherein the sterilized biodegradable poly(ethylene glycol) based insoluble hydrogel is obtained by a method comprising the steps of:
   (a) providing the hydrogel;
   (b) solvating the hydrogel in a protective solvent or in a mixture of two or more protective solvents or aqueous solutions thereof which protective solvent optionally contains one or more protecting agents; and
   (c) subjecting the solvated hydrogel to gamma radiation; wherein the protective solvent is NMP, DMA, DMF, or DMI.

2. The hydrogel of claim 1;
wherein the protective solvent is NMP.

3. The hydrogel of claim 1;
wherein sterilization is obtained with gamma radiation with a dose of from 5 to 100 kGy.

4. The hydrogel of claim 1;
wherein sterilization is obtained with gamma radiation with a dose of from 8 to 50 kGy.

5. The hydrogel of claim 1;
wherein the hydrogel is loaded with small molecule biologically active moieties.

6. The hydrogel of claim 1;
wherein the backbone moieties of the hydrogel each have a molecular weight in the range of from 1 kDa to 20 kDa.

7. The hydrogel of claim 1;
wherein the backbone moieties of the hydrogel are interconnected by hydrolytically degradable bonds; and
wherein the backbone moieties are linked together through crosslinker moieties, each crosslinker moiety being terminated by at least two of the hydrolytically degradable bonds.

8. The hydrogel of claim 1;
wherein the hydrolytically degradable bonds are carboxylic esters, carbonates, phosphoesters, or sulfonic acid esters.

9. The hydrogel of claim 1;
wherein the crosslinker moieties have a molecular weight in the range of from 60 Da to 5 kDa.

10. The hydrogel of claim 1;
wherein the backbone moieties of the biodegradable PEG based insoluble hydrogel comprise a branching core of the following formula:

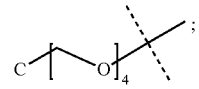

wherein the dashed line indicates attachment to the remainder of the backbone moiety.

11. The hydrogel of claim 1;
wherein the backbone moieties of the biodegradable PEG based insoluble hydrogel comprise a structure of the following formula:

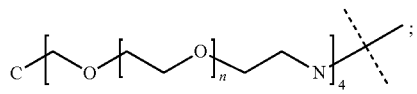

wherein:
   n is an integer of from 5 to 50; and
   the dashed line indicates attachment to the rest of the molecule.

12. The hydrogel of claim 1;
wherein the backbone moieties of the biodegradable PEG based insoluble hydrogel comprise a hyperbranched moiety Hyp.

13. The hydrogel of claim 1;
wherein the backbone moieties of the biodegradable PEG based insoluble hydrogel comprise a hyperbranched moiety Hyp of the following formula:

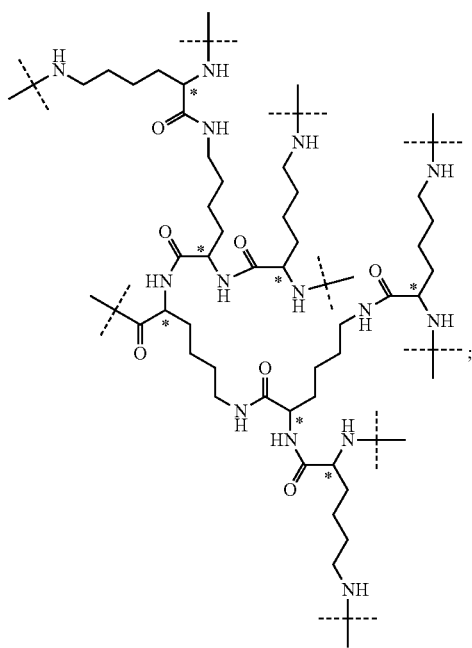

wherein:
  the dashed lines indicate attachment to the rest of the molecule; and
  carbon atoms marked with asterisks indicate S-configuration.

14. The hydrogel of claim 1;
wherein the backbone moieties are attached to at least one spacer of the following formula:

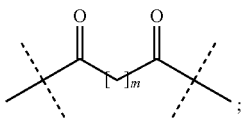

wherein one of the dashed lines indicates attachment to the hyperbranched moiety Hyp, and the second dashed line indicates attachment to the rest of the molecule; and
wherein m is an integer of from 2 to 4.

15. The hydrogel of claim 1;
wherein the backbone moieties are linked together through crosslinker moieties comprising the following structure:

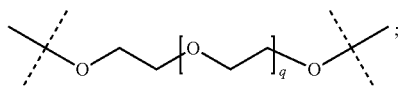

wherein q is an integer from 3 to 100.

16. The hydrogel of claim 1;
wherein the one or more protecting agents comprise at least on agent selected from the group consisting of propylamine, butylamine, pentylamine, sec. butylamine, ethanolamine, diethanolamine, serinol, trishydroxymethylaminomethane, acetic acid, formic acid, ascorbic acid, glycineamide, pivalic acid, propanoic acid, succinic acid, glutaric acid, adipic acid, thioglycerin, dithiothreitol, mercaptoethanol, and reduced glutathione.

17. A method comprising:
utilizing the hydrogel of claim 1 in tissue engineering, skin filling, an intraocular device, a medical implant, a surgical sealant or sponge, a hemostatic agent, a sustained release delivery system, a medical imaging agent, or a prodrug-carrier.

* * * * *